United States Patent [19]
Kovacevic et al.

[11] Patent Number: 4,783,405
[45] Date of Patent: * Nov. 8, 1988

[54] RECOMBINANT DNA EXPRESSION VECTORS USEFUL IN BACILLUS AND OTHER HOST CELLS

[75] Inventors: Steven Kovacevic; James R. Miller; Hansen M. Hsiung, all of Indianapolis, Ind.

[73] Assignee: Eli Lilly and Company, Indianapolis, Ind.

[*] Notice: The portion of the term of this patent subsequent to Dec. 17, 2002 has been disclaimed.

[21] Appl. No.: 654,437

[22] Filed: Sep. 26, 1984

Related U.S. Application Data

[63] Continuation-in-part of Ser. No. 458,792, Jan. 18, 1983, abandoned.

[51] Int. Cl.⁴ .................... C12P 21/00; C12N 15/00; C12N 1/20; C12N 1/00; C07H 21/00
[52] U.S. Cl. .................... 435/68; 435/172.3; 435/253; 435/320; 935/11; 935/29; 935/73; 935/74; 536/27
[58] Field of Search .................... 435/172.3, 317, 253, 435/255, 240, 68; 536/27; 935/11, 27, 29, 41, 45, 74

[56] References Cited

U.S. PATENT DOCUMENTS 4,559,300  12/1985  Kovacevic et al. ......... 435/172.3 X

FOREIGN PATENT DOCUMENTS 0036259  9/1981  European Pat. Off. ......... 435/172.3
0063953  11/1982  European Pat. Off. ......... 435/172.3

OTHER PUBLICATIONS

Murray C. et al., in *Molecular Cloning and Gene Regulation in Bacilli*, Academic Press, Inc., pp. 271–285, 1982.
Matteucci, M. et al., *Nuc. Acids Res.*, vol. 11, pp. 3113–3121, 1983.
Yansura, D. et al., in *Genetics and Biotechnology of Bacilli*, Academic Press, Inc., pp. 249–263, 1984.
Moran, C. et al., *Mol. Gen. Genetics*, vol. 186, pp. 336–346, 1982.
Palva, I. et al., *Proc. Natl. Acad. Sci.*, vol. 79, pp. 5582–5586, 1982.
Palva, I. et al., *Gene*, vol. 19, pp. 81–87, 1982.
Kovacevic, S. et al., *J. Bacteriol*, vol. 162, pp. 521–528, 1985.
Shortle, D., *Gene*, vol. 22, pp. 181–189, 1983.

*Primary Examiner*—Thomas G. Wiseman
*Assistant Examiner*—Jayme A. Huleatt
*Attorney, Agent, or Firm*—Gerald V. Dahling; Leroy Whitaker

[57] ABSTRACT

Recombinant DNA expression vectors for use in Bacillus and other host cells are disclosed. The vectors comprise the veg promoter sequence of *Bacillus subtilis*, a novel ribosome binding site-containing sequence and a sequence that codes for a functional polypeptide. The ribosome binding site-containing sequence is synthesized in accordance with conventional procedures while the veg promoter sequence can be obtained from *E. coli* K12 JA221/pMS480 (NRRL B-15258). Various sequences that codes for functional polypeptides and method for their expression in Bacillus are also disclosed.

87 Claims, 7 Drawing Sheets

Restriction Site Map of Plasmids pOW 525, pOW 526, pOW 527 and pOW 528

1. pOW 525 (~8.4 kb)
2. pOW 526 (~8.4 kb)
3. pOW 527 (~12.8 kb)
4. pOW 528 (~12.8 kb)

Restriction Site Map of Plasmids pOW 523, pOW 524, pOW 529 and pOW530**

1. pOW 523 ~ 14.2 kb
2. pOW 524 ~ 14.2 kb
3. pOW 529 ~ 18.6 kb
4. pOW 530 ~ 18.6 kb

Synthesis Procedure for Fragment T₁

Restriction Site Map of Plasmids pEL 107 and pEL 105 pEL107 pEL105

Restriction Site Map of Plasmids pBS 1 and pBS 3 pBS 1 pBS 3

Restriction Site Map of
Plasmid pOW441

Restriction Site Map of
Plasmid pOW445

RECOMBINANT DNA EXPRESSION VECTORS USEFUL IN BACILLUS AND OTHER HOST CELLS

CROSS-REFERENCE

This application is a continuation-in-part of U.S. patent application Ser. No. 458,792, filed Jan. 18, 1983.

SUMMARY OF THE INVENTION

The present invention comprises novel recombinant DNA expression vectors which comprise a *Bacillus subtilis* ribosome binding site-encoding DNA fragment ligated both to the veg promoter of *B. subtilis* and also to a gene that encodes a functional polypeptide. The invention further comprises transformants of the aforementioned vectors and also a method for producing a functional polypeptide wherein the polypeptide is produced in Bacillus and secreted into the growth medium.

The present invention provides expression vectors for use in Bacillus and other host cells. Heretofore, the development and exploitation of recombinant DNA technology in Bacillus has been retarded and made especially difficult because of the general lack of suitable cloning and expression vectors. This paucity of expression vectors is explained in part by the lack of recognition afforded foreign transcription and translation initiation signals in Bacillus. Consequently, the well known trp (Hallewell, R. A. and S. Emtage, 1980, Gene 9:27), lac (Guarante, L. et al., 1980, Cell 20:543 and Roberts, T. M. et al., 1979, Proc. Nat. Acad. Sci. USA 76:5596), lpp (Lee, N. et al., 1981, J. of Bacteriol. 146:861; Zwiebel, L. J. et al., 1981, J. of Bacteriol. 145:654 and Nakamura, K. and M. Inouye, 1979, Cell 18:1109) and Bacteriophage $\lambda P_L$ (Derom, C. et al., 1982, Gene 17:45; Remaut, E. et al., 1981, Gene 15(1):81 and Bernard, H. et al., 1979, Gene 5:59) transcription and translation-directing promoter systems are not functional in Bacillus. Thus, with the exception of a few drug resistance genes from gram positive organisms such as Staphylococcus and Streptococcus, few foreign and practically no eukaryotic genes have been expressed in Bacillus.

The extremely limited ability of Bacillus to recognize foreign transcription and translation signals necessitates the development of endogenous signals that direct gene expression. Several early cloning attempts include the cloning and expression of the *B. licheniformis* beta-lactamase gene, (disclosed in European Patent Office Publication (of European Patent Application No. 81300858.8) No. 0036259) and the *B. stearothermophilus* and *B. amylolicuefaciens* α-amylase genes, (respectively disclosed in European Patent Office Publication (of European Patent Application No. 82300158.1) No. 0057976 and Derwent Abstract (of Belgium Patent Application No. BE 891-659) No 37323 E/19) in *B. subtilis*. In addition, the veg promoter and translation signals (endogenous to *B. subtilis* and disclosed in Moran Jr., C. P. et al., 1982, Mol. Gen. Genet. 186:339), have also been isolated and are useful as a starting material for purposes of constructing the present invention. Accordingly, the aforementioned veg promoter- and translation signal-containing sequence was modified and engineered to be useful for directing the expression of virtually any polypeptide in Bacillus. This represents a significant advance in the technical art and helps fill the need for expression vectors which are useful in gram positive microorganisms.

Gene cloning and expression of products in *Bacillus subtilis* are highly advantageous since the organism is non-pathogenic, does not produce endotoxins and can secrete gene products into the growth medium. In addition, *B. subtilis* has been extensively studied and is the archetype for genetic studies among gram positive micrcorganisms. The small and versatile expression vectors of the present invention are particularly important because they allow for the commercial exploitation of these important advantages.

For purposes of the present invention, as disclosed and claimed herein, the following terms are as defined below.

Recombinant DNA Expression Vector—any autonomously replicating agent, including but not limited to plasmids, comprising a DNA molecule to which one or more additional DNA segments can or have been added.

Transformation—the introduction of DNA into a recipient host cell that changes the genotype and consequently results in a change in the recipient cell. Transformant—a recipient host cell that has undergone transformation.

Restriction Fragment—any linear portion or whole of plasmid or chromosomal DNA generated by the action of one or more restriction enzymes.

Functional Polypeptide—a recoverable bioactive entirely heterologous polypeptide or precursor, a recoverable bioactive polypeptide comprising a heterologous polypeptide and a portion or whole of a homologous polypeptide, or a recoverable bioinactive fusion polypeptide comprising a heterologous polypeptide and a bioinactivating homologous polypeptide which can be specifically cleaved.

Fused Gene Product—a recoverable heterologous polypeptide which is fused with a portion or whole of a homologous polypeptide.

Insertional Isomer—one of the two or more possible recombinant DNA molecules formed when a DNA fragment is inserted at one of two or more compatible sites on the recipient DNA.

DETAILED DESCRIPTION OF THE INVENTION

Figure 1:
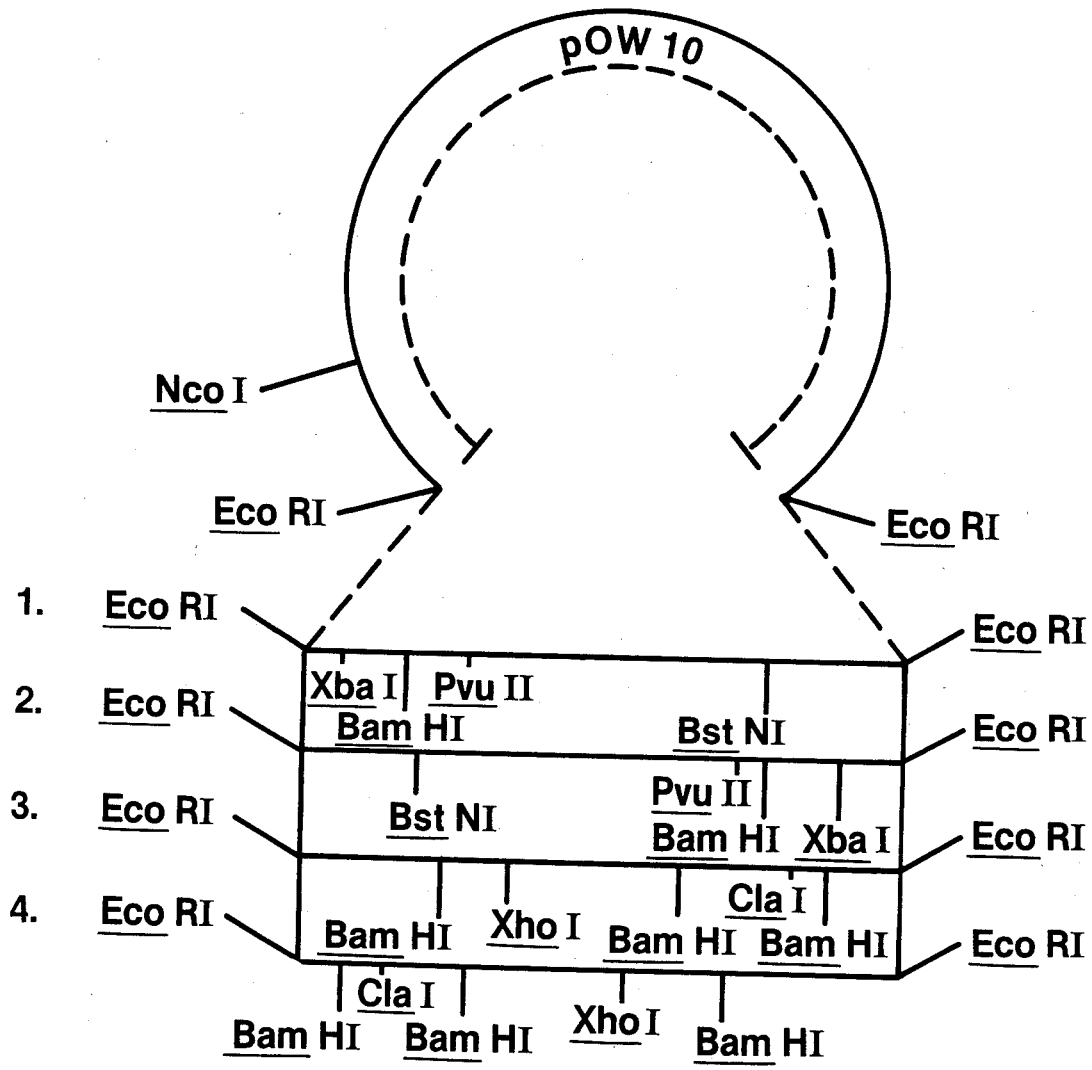

The present invention comprises novel recombinant DNA expression vectors which comprise (1) the ribosome binding site-containing DNA sequence

wherein
A is deoxyadenyl,
G is deoxyguanyl,
C is deoxycytosyl,
T is thymidyl,
R is G or C, and
$R^1$ is G or C, (2) the veg promoter of *Bacillus subtilis*, and (3) a gene that encodes a functional polypeptide, subject to the limitation that R and $R^1$ are not simultaneously the same deoxyribonucleotide and subject to the further limitation that said vector is selectable and that said promoter and said DNA sequence direct transcription and expression of said gene in a host cell transformed by said vector. The invention further comprises transformants of the aforementioned vectors and also a method for producing a functional polypeptide wherein the polypeptide is produced in Bacillus and secreted into the culture medium.

The ribosome binding site-containing DNA sequence to which the veg promoter and gene are ligated can be conventionally synthesized by the modified phosphotriester method, using fully protected trideoxyribonucleotide building blocks, in substantial accordance with the procedures of Itakura et al., 1977, Science 198:1056 and Crea et al., 1978, Proc. Nat. Acad. Sci. USA 75:5765. The veg promoter can either be synthesized directly or obtained by EcoRI-SfaNI digestion of plasmid pMS480. The resultant ~0.38 kb EcoRI-SfaNI fragment contains the veg promoter as well as additional deoxyribonucleotides at the 5' end of the coding strand (adjacent to the EcoRI sticky terminus). Plasmid pMS480 is ~4.8 kb and can be conventionally isolated from *E. coli* K12 JA221/pMS480, a strain deposited and made part of the permanent stock culture collection of the Northern Regional Research Laboratory, Peoria, Illinois. The strain is available to the public as a preferred source and stock reservoir of plasmid pMS480 under the accession number NRRL B-15258.

For convenience and ease of construction, the veg promoter was obtained by EcoRI-SfaNI digestion of plasmid pMS480. The resultant fragment was then ligated to the aforedescribed ribosome binding sitecontaining DNA sequence, a sequence designed to have SfaNI and NcoI sticky ends. The sequence thus allows for the direct expression of a polypeptide upon simultaneous ligation with both a NcoI-restricted gene and the aforementioned ~0.38 kb EcoRI-SfaNI veg promoter-containing fragment. Direct expression results because the ligation of the NcoI sticky ends restores the ATG translational start triplet of the NcoI-restricted gene. The synthetic sequence is therefore useful for the universal direct expression, under the control of the *Bacillus subtilis* veg promoter, of any gene that encodes a functional polypeptide.

Although genes that naturally contain a NcoI site at the translational start point are preferred, genes lacking such sites can also be used. In the latter case, the gene can be cleaved by a restriction enzyme and then reconstructed synthetically (Itakura et al., 1977 and Crea et al., 1978) so as to contain the desired NcoI sticky end. Alternatively, depending upon convenience and ease of construction, the modified gene may be entirely synthetic. In either case, the modified gene can be ligated to the NcoI sticky end of the aforementioned ribosome binding site-containing sequence thus restoring the ATG methionine-encoding start triplet and thus allowing for the direct expression of a desired product. The Bacillus promoter-containing expression vectors of the present invention represent a significant technical advance. They are universally applicable in Bacillus and can be used for the expression, under the control of a homologous Bacillus promoter, of any polypeptide-encoding gene.

Expression vectors illustrative of the present invention were constructed by ligating the ~0.38 kb EcoRI-SfaNI fragment of plasmid pMS480, the ~0.4 kb EcoRI-NcoI fragment of the pre-proinsulin plasmid pOW601 and the aforementioned ribosome binding sitecontaining DNA sequence. The resultant plasmid, designated as pOW10, is functional in *E. coli* and comprises a functional polypeptide-encoding gene in translational reading phase with the veg promoter. Plasmid pOW10 is particularly useful for constructing illustrative expression vectors that are functional in Bacillus. Plasmid pOW601, which is used as a starting material for constructing plasmid pOW10, is ~4.4 kb and can be conventionally isolated from *E. coli* K12 JA221/pOW601, a strain deposited and made part of the permanent stock culture collection of the Northern Regional Research Laboratory, Peoria, Ill. The strain is available to the public as a preferred source and stock reservoir of the plasmid under the accession number NRRL B-15259.

Illustrative vectors that are functional in Bacillus are constructed by ligating EcoRI-digested plasmid pOW10 into EcoRI-digested plasmid pHI-18 or pBSl. Plasmid pHI-18 is ~3.9 kb and contains a chloramphenicol resistance gene as well as an origin of replication that is functional in Bacillus. Plasmid pHI-18 is constructed by an ~0.7 kb HpaII deletion of plasmid pHI-16. The latter plasmid is an in vivo deletion of known chimeric plasmid pBD12 (disclosed in Gryczan et al., 1980, J. Bacteriology 141(1):246) which can be conventionally isolated from *Bacillus subtilis* MI112/pHI-16, a constructed strain deposited and made part of the permanent stock culture collection of the Northern Regional Research Laboratory, Peoria, Ill. The strain is available to the public as a preferred source and stock reservoir of the plasmid under the accession number NRRL B-12597. The aforementioned ligation into plasmid pHI-18 results in the illustrative ~8.4 kb plasmids pOW525 and pOW526. A restriction site map of each of plasmids pOW525 and pOW526 is presented in FIG. 1 of the accompanying drawings.

Ligation of EcoRI-digested plasmid pOW10 into EcoRI-digested plasmid pBSI results in the illustrative ~12.8 kb plasmids pOW527 and pOW528. Plasmid pBSI is constructed by ligating the ~4.6 kb BamHI fragment of plasmid pHI-18 into the ~4.4 kb BamHI fragment of plasmid pEL105. Plasmid pEL105 is constructed by ligating the ~1.6 kb BamHI fragment of plasmid pLR2 (constructed by ligating HindIII-digested plasmid pIJ6 (disclosed in Thompson et al., 1980, Nature 286:525), and HindIII-digested plasmid pBR322), into the ~2.8 kb BamHI fragment of plasmid pEL103. The latter plasmid can be conventionally isolated from *Streptomyces granuloruber* No. A39912.13/pEL103, a strain deposited and made part of the permanent stock culture collection of the Northern Regional Research Laboratory, Peoria, Ill. The strain is available as a preferred source and stock reservoir of the plasmid under the accession number NRRL 12549. A restriction site map of each of plasmids pOW527 and pOW528 is presented in FIG. 1 of the accompanying drawings.

Plasmids pOW525, pOW526, pOW527 and pOW528 are functional in Bacillus, comprise a functional pre-pro- insulin-encoding gene in translational reading phase with the veg promoter and ribosome binding site-containing synthetic DNA sequence and therefore exemplify the present invention. Other illustrative vectors were constructed by (1) digesting plasmid pOW10 with NcoI and plasmid pMC1403 with BamHI restriction enzyme; (2) filling in the resulting sticky ends with the Klenow fragment of DNA polymerase; (3) digesting the filled-in fragments with EcoRI restriction enzyme and (4) ligating the resultant two fragments at their respective EcoRI and blunted ends. Plasmid pMC1403, which is used as a starting material for these constructions, is ~9.9 kb and contains a portion of the lacZ gene. The plasmid can be conventionally isolated from *E. coli* K12 BE904/pMC1403, a strain deposited and made part of the permanent stock culture collection of the Northern Regional Research Laboratory, Peoria Ill. The strain is available to the public as a preferred source and stock reservoir of the plasmid under the accession number NRRL B-15213. The aforementioned ligation restores both the NcoI and BamHI restriction sites and therefore results in a plasmid, designated as plasmid pOW303, which contains a portion of the lacZ gene in translational reading phase with the veg promoter and ribosome binding site-containing synthetic DNA sequence.

Figure 2:
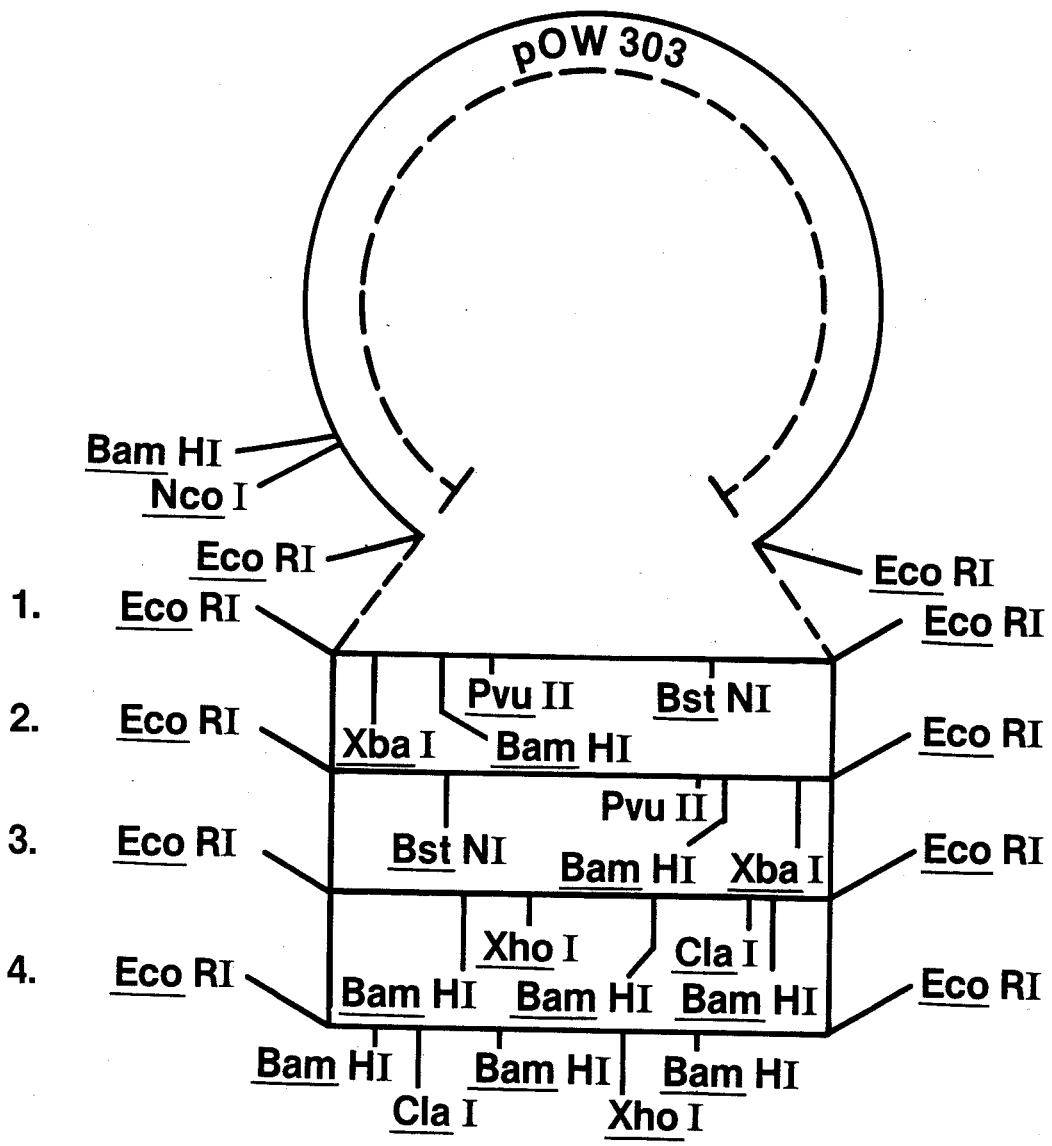

Plasmid pOW303 was digested with EcoRI restriction enzyme and ligated to EcoRI-digested plasmid pHI-18 to produce the illustrative plasmids pOW523 and pOW524. A similar construction, involving the substitution of EcoRI-digested plasmid pBS1 for the EcoRIdigested plasmid pHI-18, results in illustrative plasmids pOW529 and pOW530. Plasmids pOW523, pOW524, pOW529 and pOW530 are functional in Bacillus, comprise a functional polypeptide-encoding gene in translational reading phase with the veg promoter and aforementioned DNA sequence and therefore further illustrate the present invention. The β-galactosidase activity conferred to host cells by the aforementioned vectors can be employed as a selectable marker making the vectors generally useful for molecular cloning. Restriction site maps of plasmids pOW523, pOW524, pOW529 and pOW530 are presented in FIG. 2 of the accompanying drawings.

Additional plasmids wherein the aforedescribed veg promoter and ribosome binding site-containing DNA directs the expression of the Staphylococcus nuclease gene can be constructed to further exemplify the present invention. The aforementioned nuclease structural gene was isolated as a single Sau3A fragment of 518 base pairs (bp) from plasmid pOW440. Plasmid pOW440 can be obtained from *Bacillus subtilis* MI112-/pOW440, a strain deposited and made part of the permanent stock culture collection of the Northern Regional Research Laboratory, Peoria, Ill. The strain is available to the public as a preferred source and stock reservoir of plasmid pOW440 under the accession number NRRL B-15887.

The Sau3A fragment was ligated into BamHI-digested plasmid pOW303 disrupting the expression of β-galactosidase and resulting in plasmid pOW323/Z. Upon ligation into the BamHI site, the amino-terminus Sau3A site was reconstituted as a BamHI site. The entire sequence of interest (plus about 100 bp of the lacZ gene) was isolated on a single EcoRI-PvuII fragment of plasmid pOW323/Z and then ligated with the origin of replication and ampicillin resistance gene-containing EcoRI-PvuII fragment of plasmid pBR322. The resultant plasmid, designated as plasmid pOW323, contains a single NcoI site overlapping the aforementioned BamHI site. Therefore, the relevant sequence is (only one strand shown for convenience)

<u>met asp pro</u>

Figure 6:
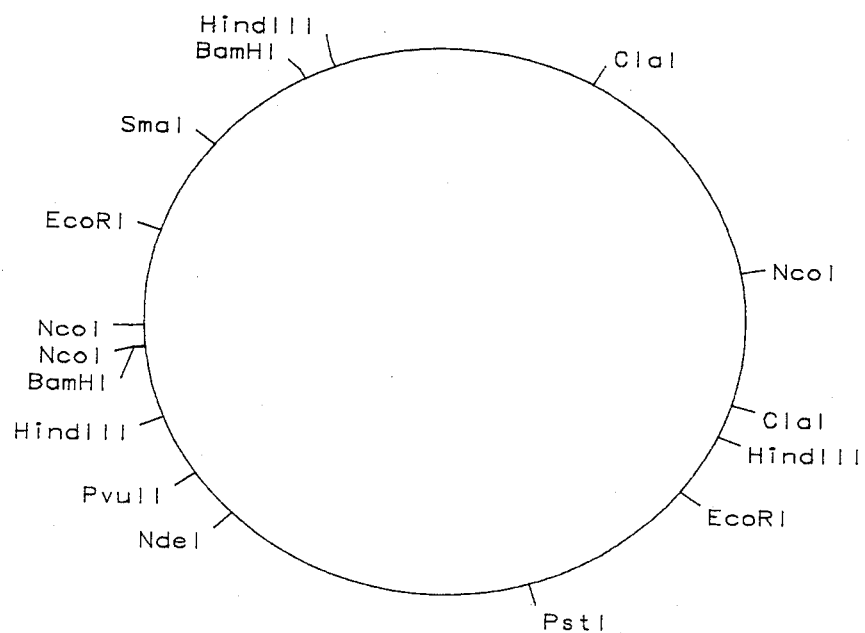

CC—ATG GAT CCA followed immediately by the remainder of the nuclease coding sequence. Finally, a chemically synthesized fragment coding for the met-val analogue of the α-amylase signal peptide from *Bacillus amyloliquefaciens* (Palva et al., 1981, Gene 15:43) was inserted. The plasmid DNA from one clone which produced nuclease in *E. coli* was sequenced, determined to have the synthesized signal sequence intact and in proper orientation and was designated as plasmid pOW324. To shuttle plasmid pOWE24 between *E. coli* and *Bacillus*, plasmid pOW324 was opened at its unique EcoRI site and ligated into EcoRI-cut plasmid pOW430 to yield plasmid pOW441. The plasmid pOW430 starting material is a Bacillus cloning vector that can be obtained from *Bacillus subtilis* MI112/pOW430, a strain deposited and made part of the permanent stock culture collection of the Northern Regional Research Laboratory, Peoria, Ill. The strain is available to the public as a preferred source and stock reservoir of plasmid pOW430 under the accession number NRRL B-15833. The Bacillus transformants of plasmid pOW441 were shown to express and secrete the Staphylococcus nuclease enzyme in large amounts. A restriction site map of plasmid pOW441 is presented in FIG. 6 of the accompanying drawings.

Figure 7:
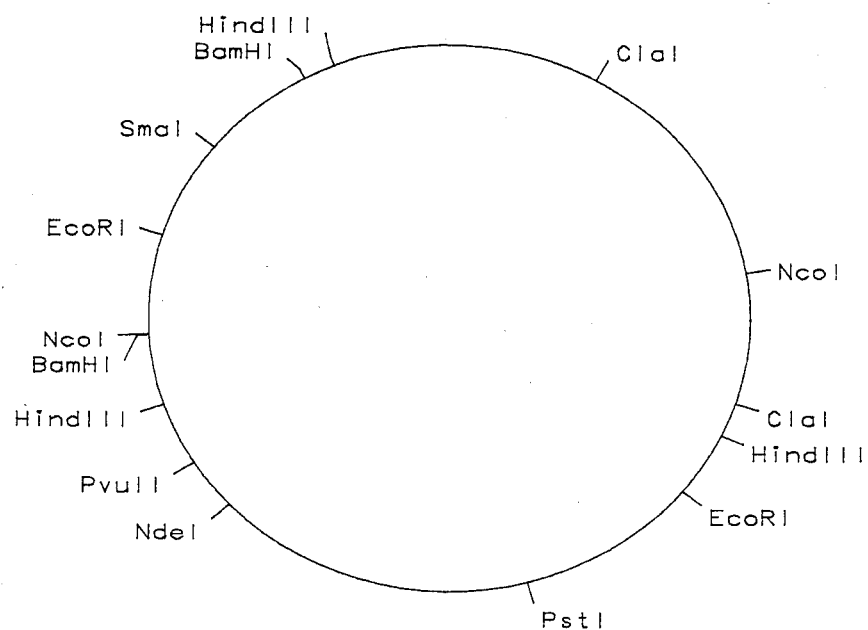

A structurally related plasmid, designated as plasmid pOW445, was also constructed to further exemplify the present invention. The plasmid is similar to plasmid pOW441 except that the α-amylase signal sequence is deleted. The Bacillus transformants of plasmid pOW445 were also shown to express the Staphylococcus nucleaase enzyme in large amounts. A restriction site map of plasmid pOW445 is presented in FIG. 7 of the accompanying drawings.

The present invention also provides a method for producing a functional polypeptide in Bacillus wherein said polypeptide is secreted into the culture medium. Secretion occurs when the polypeptide-encodsequenceing gene of the present invention also encodes a signal peptide. Signal peptides are short leader regions of amino acids which often comprise newly synthesized polypeptides and which are believed to function in the transport of polypeptides across cell membranes. Signal peptides are typically cleaved from the newly synthesized polypeptides during transport. The aforementioned method for secretion, which is in no way limited by the underlying transport mechanism, comprises transforming a Bacillus host cell with a recombinant DNA expression vector which comprises (1) the ribosome binding site-containing DNA sequence

wherein
A is deoxyadenyl,
G is deoxyguanyl,
C is deoxycytosyl,
T is thymidyl,
R is G or C, and
$R^1$ is G or C, (2) the veg promoter of Bacillus subtilis, and (3) a gene that encodes a signal peptide-containing functional polypeptide, and culturing said transformed Bacillus host cell under growth conditions, subject to the limitation that R and $R^1$ are not simultaneously the same deoxyribonucleotide and subject to the further limitation that said vector is selectable and that said promoter and said DNA sequence direct transcription and expression of said gene in said transformed Bacillus cell.

Plasmids pOW525, pOW526, pOW527, pOW528 and pOW441 and the Bacillus subtilis MI112 transformants thereof, exemplify the present method for secretion. The plasmids each comprise the aforedescribed veg promoter, ribosome binding site-containing DNA sequence and a gene that encodes pre-proinsulin (the signal peptide-containing form of proinsulin), or the Staphylococcus nuclease gene linked to the α-amylase signal sequence. When *Bacillus subtilis* host cells are transformed by these vectors, pre-proinsulin or Staphylococcus nuclease are produced intracellularly with secretion into the culture medium.

The aforementioned method for secretion is not limited to the use of genes encoding pre-proinsulin or Staphylococcus nuclease. Any gene that codes for a signal peptide-containing functional polypeptide can be used including, for example, genes that code for immune modulators, pregrowth hormone, pre-human growth hormone, pre-porcine growth hormone, proteolytic degradative enzymes and cellulolytic degradative enzymes. Moreover, DNA encoding a given signal peptide can be synthesized directly or cleaved from pre-existing genes and then ligated to genes that normally lack such signal peptide-encoding sequences. In this way, any gene that encodes a functional polypeptide can be modified such that the present method for secretion can be applied. Thus, the present method is not limited to the use of genes that naturally contain a signal peptide-encoding region. The present invention is particularly versatile and can be applied to the production of any polypeptide which can be encoded by a gene in a recombinant DNA cloning vector. A preferred recombinant DNA cloning vector is the plasmid although bacteriophage and other vectors can also be used and are apparent to those skilled in the art. In addition to the illustrative pre-proinsulin and lacZ genes, other genes that can be used include genes that are naturally occurring, genes that are non-naturally occurring and genes that are in part naturally occurring and in part synthetic or non-naturally occurring. More particularly, the genes can code for human proinsulin, human insulin A-chain, human insulin B-chain, non-human insulin, human growth hormone, non-human growth hormone, bovine growth hormone, porcine growth hormone, human interferon, non-human interferon, viral antigen, urokinase, any peptide hormone, any enzyme or virtually any other polypeptide with research or commercial value.

The recombinant DNA expression vectors of the present invention are not limited for use in a single species or strain. To the contrary, the vectors are broadly applicable and can be transformed into host cells of many taxa, particularly the restrictionless strains of Bacillus, Streptomyces and *E. coli*. Restrictionless strains are readily selected and isolated from Bacillus and Streptomyces taxa by conventional procedures and extensions of principles well known in the art (Lomovskaya et al., 1980, Microbiological Reviews 44:206). Host cells of restrictionless strains lack restriction enzymes and therefore do not cut or degrade plasmid DNA upon transformation. For purposes of the present application, host cells containing restriction enzymes that do not cut any of the restriction sites of the present vectors are also considered restrictionless.

Preferred host cells of restrictionless strains of Bacillus, in which the present vectors are especially useful and can be transformed, include restrictionless cells of, for example, *B. subtilis*, *B. subtilis* MI112, *B. thuringiensis*, *B. thuringiensis* var. *israeliensis*, *B. cereus*, *B. anthracis*, *B. piliformis*, *B. tropicus*, *B. alvei*, *B. megaterium*, *B. pumilus*, *B. licheniformis*, *B. polymyxa*, *B. macerans*, *B. circulans*, *B. stearothermophilus*, *B. coagulans*, *B. firmus*, *B. brevis*, *B. sphaericus*, *B. pasteurii*, *B. fastidiosus*, *B. larvae*, *B. lentimorbus*, *B. apiarus*, *B. amyloliquifaciens*, *B. laterosporus*, and *B. popillae*.

Preferred host cells of restrictionless strains of Streptomyces taxa that produce aminoglycoside antibiotics and in which the present vectors are especially useful and can be transformed, include restrictionless cells of, for example: *S. kanamyceticus* (kanamycins), *S. chrestomyceticus* (aminosidine), *S. griseoflavus* (antibiotic MA 1267), *S. microsporeus* (antibiotic SF-767), *S. ribosidificus* (antibiotic SF733), *S. flavopersicus* (spectinomycin), *S. spectabilis* (actinospectacin), *S. rimosus* forma *paromomycinus* (paromomycins, catenulin), *S. fradiae* var. *italicus* (aminosidine), *S. bluensis* var. *bluensis* (bluensomycin), *S. catenulae* (catenulin), *S. olivoreticuli* var. *cellulophilus* (destomycin A), *S. tenebrarius* (tobramycin, apramycin), *S. lavendulae* (neomycin), *S. albogriseolus* (neomycins), *S. albus* var. *metamycinus* (metamycin), *S. hygroscopicus* var. *sagamiensis* (spectinomycin), *S. bikiniensis* (streptomycin), *S. griseus* (streptomycin), *S. erythrochromogenes* var. *narutoensis* (streptomycin), *S. poolensis* (streptomycin), *S. galbus* (streptomycin), *S. rameus* (streptomycin), *S. olivaceus* (streptomycin), *S. mashuensis* (streptomycin), *S. hygroscopicus* var. *limoneus* (validamycins), *S. rimofaciens* (destomycins), *S. hygroscopicus* forma *glebosus* (glebomycin), *S. fradiae* (hybrimycins neomycins), *S. eurocidicus* (antibiotic A16316C), *S. aquacanus* (N-methyl hygromycin B), *S. crystallinus* (hygromycin A), *S. noboritoensis* (hygromycin), *S. hygroscopicus* (hygromycins), *S. atrofaciens* (hygromycin), *S. kasugaspinus* (kasugamycins), *S. kasugaensis* (kasugamycins), *S. netropsis* (antibiotic LL-AM31), *S. lividus* (lividomycins), *S. hofuensis* (seldomycin complex), and *S. canus* (ribosyl paromamine).

Preferred host cells of restrictionless strains of Streptomyces taxa that produce macrolide antibiotics and in which the present vectors are especially useful and can be transformed, include restrictionless cells of, for example: *S. caelestis* (antibiotic M188), *S. platensis* (platenomycin), *S. rochei* var. *volubilis* (antibiotic T2636), *S. venezuelae* (methymycins), *S. griseofuscus* (bundlin), *S. narbonensis* (josamycin, narbomycin), *S. fungicidicus* (antibiotic NA-181), *S. griseofaciens* (antibiotic PA133A, B), *S. roseocitreus* (albocycline), *S. bruneogriseus* (albocycline), *S. roseochromogenes* (albocycline), *S. cinerochromogenes* (cineromycin B), *S. albus* (albomycetin), *S. felleus* (argomycin, picromycin), *S. rochei* (lankacidin, borrelidin), *S. violaceoniger* (lankacidin), *S. griseus* (borrelidin), *S. maizeus* (ingramycin), *S. albus* var. *coilmyceticus* (coleimycin), *S. mycarofaciens* (acetyl-leukomycin, espinomycin), *S. hygroscopicus* (turimycin, relomycin, maridomycin, tylosin, carbomycin), *S. griseospiralis* (relomycin), *S. lavendulae* (aldgamycin), *S. rimosus* (neutramycin), *S. deltae* (deltamycins), *S. fungicidicus* var. *espinomyceticus* (espinomycins), *S. furdicidicus* (mydecamycin), *S. ambofaciens* (foromacidin D), *S. eurocidicus* (methymycin), *S. griseolus* (griseomycin), *S. flavochromogenes* (amaromycin, shincomycins), *S. fimbriatus* (amaromycin), *S. fasciculus* (amaromycin), *S. erythreus* (erythromycins), *S. antibioticus* (oleandomycin), *S. olivochromogenes* (oleandomycin), *S. spinichromogenes* var. *suragaoensis* (kujimycins), *S. kitasatoensis* (leucomycin), *S. narbonensis* var.

*josamyceticus* (leucomycin A3, josamycin), *S. albogriseolus* (mikonomycin), *S. bikiniensis* (chalcomycin), *S. cirratus* (cirramycin), *S. djakartensis* (niddamycin), *S. eurythermus* (angolamycin), *S. fradiae* (tylosin, lactenocin, macrocin), *S. goshikiensis* (bandamycin), *S. griseoflavus* (acumycin), *S. halstedii* (carbomycin), *S. tendae* (carbomycin), *S. macrosporeus* (carbomycin), *S. thermotolerans* (carbomycin), and *S. albireticuli* (carbomycin).

Preferred host cells of restrictionless strains of Streptomyces taxa that produce β-lactam antibiotics and in which the present vectors are especially useful and can be transformed, include restrictionless cells of, for example: *S. lipmanii* (A16884, MM4550, MM13902), *S. clavuligerus* (A16886B, clavulanic acid), *S. lactamdurans* (cephamycin C), *S. griseus* (cephamycin A, B), *S. hygroscopicus* (deacetoxycephalosporin C), *S. wadayamensis* (WS-3442-D), *S. chartreusis* (SF 1623), *S. heteromorphus* and *S. panayensis* (C2081X); *S. cinnamonensis, S. fimbriatus, S. halstedii, S. rochei* and *S. viridochromogenes* (cephamycins A, B); *S. cattleya* (thienamycin); and *S. olivaceus, S. flavovirens, S. flavus, S. fulvoviridis, S. argenteolus,* and *S. sioyaensis* (MM 4550 and MM 13902).

Preferred host cells of restrictionless strains of Streptomyces taxa that produce polyether antibiotics and in which the present vectors are especially useful and can be transformed, include restrictionless cells of, for example: *S. albus* (A204, A28695A and.B, salinomycin), *S. hygroscopicus* (A218, emericid, DE3936), A120A, A286-95A and B, etheromycin, dianemycin), *S. griseus* (griso-rixin), *S. conglobatus* (ionomycin), *S. eurocidicus* var. *asterocidicus* (laidlomycin), *S. lasaliensis* (lasalocid), *S. ribosidificus* (lonomycin), *S. cacaoi* var. *asoensis* (lysocellin), *S. cinnamonensis* (monensin), *S. aureofaciens* (narasin), *S. gallinarius* (RP 30504), *S. longwoodensis* (lysocellin), *S. flaveolus* (CP38936), *S. mutabilis* (S-11743a), and *S. violaceoniger* (nigericin).

Preferred host cells of restrictionless strains of Streptomyces taxa that produce glycopeptide antibiotics and in which the present vectors are especially useful and can be transformed, include restrictionless cells of, for example: *S. orientalis* and *S. haranomachiensis* (vancomycin); *S. candidus* (A-35512, avoparcin), and *S. eburosporeus* (LL-AM 374).

Preferred host cells of other Streptomyces restrictionless strains in which the present vectors are especially useful and can be transformed, include restrictionless cells of, for example: *S. coelicolor, S. granuloruber, S. roseosporus, S. lividans, S. espinosus* and *S. azureus.*

The invention is not limited for use in Bacillus and Streptomyces but can also be used in various *E. coli* host cells. Preferred *E. coli* host cells include, but are not limited to, *E. coli* K12, *E. coli* K12 JA221, *E.coli* K12 HB101, *E. coli* K12 C600, *E. coli* K12 C600M$_k^-$R$_k^-$, *E. coli* K12 C600M$^+$R$_k^-$ and *E. coli* K12 RV308.

While all the embodiments of the present invention are useful, some of the present expression vectors are preferred. Accordingly, preferred vectors are plasmids pOW523, pOW524, POW525, pOW526, pOW527, pOW528, pOW529, pOW530, pOW441 and pOW445 and preferred transformants are *Bacillus subtilis* MI112/pOW523, *B. subtilis* MI112/pOW524, *B. subtilis* MI112/pOW525, *B. subtilis* MI112/pOW526, *B. subtilis* MI112/pOW527, *B. subtilis* MI112/pOW528, *B. subtilis* MI112/pOW529, *B. subtilis* MI112/pOW530, *B. subtilis* MI112/pOW441 and *B. subtilis* MI112/pOW445. Of this preferred group, plasmids pOW523, pOW525, pOW527, pOW529, pOW441 and pOW445 and transformants *B. subtilis* MI112/pOW523, *B. subtilis* MI112/pOW525, *B. subtilis* MI112/pOW527, *B. subtilis* MI112/pOW529, *B. subtilis* MI112/pOW441 and *B. subtilis* MI112/pOW445 are most preferred.

The recombinant DNA expression vectors and transformants of the present invention have broad utility and help fill the need for expression vehicles, especially for use in Bacillus. Thus, the present vectors allow for the genetic expression and secretion in Bacillus of products now bioproduced in *E. coli*. This is especially advantageous because large scale fermentation of Bacillus is better known and understood than is fermentation of *E. coli*. In fact, commercial fermentation of *E. coli* is still highly experimental and fraught with difficulty. The present invention circumvents this problem by providing the alternative of producing compounds now biosynthesized in *E. coli* such as, for example, human insulin, human proinsulin, glucagon, interferon, human growth hormone, bovine growth hormone and the like, in Bacillus. This can be done because the present vectors are highly versatile and can accommodate DNA sequences which encode the aforementioned products. Thus, the present invention allows for flexibility in the choice of hosts and provides a means for using Bacillus in the bioproduction of polypeptides and other gene products.

The ability of the present transformants to secrete polypeptide products is commercially advantageous. For example, isolation and purification of polypeptides can be done continuously during fermentation without the lytic destruction of host cells. Secretion also affords protection against proteolytic degradation of gene products by naturally occurring protease enzymes. Microorganisms are notorious for producing such enzymes which rapidly digest unprotected foreign polypeptides. The present method for secretion circumvents this problem by providing a means for removing susceptible polypeptides from the host cell before proteolytic degradation can occur. In addition, host cells are also protected from the toxic effects of a given gene product since secretion out of the cell prevents the deleterious effects and possible cell death associated with intracellular build-up.

*Streptomyces granuloruber* No. A39912.13/pEL103, *Bacillus subtilis*/MI112/pHI-16, *E. coli* K12 JA221/pMS480, *E. coli* K12 BE904/pMC1403, *E. coli* K12 JA221/pOW601, *Bacillus subtilis* MI112/pOW430 and *Bacillus subtilis* MI112/pOW440, as respective sources of plasmids pEL103, pHI-16, pMS480, pMC1403, pOW601, pOW430 and pOW440, and *Streptomyces ambofaciens* can be cultured in a number of ways using any of several different media. Carbohydrate sources which are preferred in a culture medium include, for example, molasses, glucose, dextrin, and glycerol, and nitrogen sources include, for example, soy flour, amino acid mixtures, and peptones. Nutrient inorganic salts are also incorporated and include the customary salts capable of yielding sodium, potassium, ammonium, calcium, phosphate, chloride, sulfate, and like ions. As is necessary for the growth and development of other microorganisms, essential trace elements are also added. Such trace elements are commonly supplied as impurities incidental to the addition of other constituents of the medium.

*Streptomyces granuloruber* No. A39912.13/pEL103 is grown under aerobic culture conditions over a relatively wide pH range of about 5 to 9 at temperatures ranging from about 15° to 40° C. For production of plasmid pEL103 in the greatest quantity, however, it is desirable to start with a culture medium at a pH of about 7.2 and maintain a culture temperature of about 30° C. Culturing *Streptomyces granuloruber* No. A39912.13/pEL103, under the aforementioned conditions, results in a reservoir of cells from which plasmid pEL103 is isolated conveniently by techniques well known in the art.

*Bacillus subtilis* MI112/pHI-16, *B. subtilis* MI112/pOW430 and *B. subtilis* MI112/pOW440 are grown under aerobic culture conditions over a relatively wide pH range of about 5 to 8.5 at temperatures ranging from about 25° to 45° C. For production of plasmids pHI-16, pOW430, and pOW440 in the greatest quantity, however, it is desirable to start with a culture medium at a pH of about 7 and maintain a culture temperature of about 37° C. Culturing *B. subtilis* MI112/pHI-16, *B. subtilis* MI112/pOW430 and *B. subtilis* MI112/pOW440, under the aforementioned conditions, results in a reservoir of cells from which plasmids pHI-16, pOW430 and pOW440 are isolated conveniently by techniques well known in the art.

*E. coli* K12 JA221/pMS480, *E. coli* K12 BE904/pMC1403 and *E. coli* K12 JA221/pOW601 are each grown under aerobic culture conditions over a relatively wide pH range of about 6.5 to 8 at temperatures ranging from about 25° to 40° C. For production of plasmids pMS480, pMC1403, pOW601, pOW430 and pOW440 in the greatest quantity, however, it is desirable to start with a culture medium at a pH of about 7.2 and maintain a culture temperature of about 37° C. Culturing the *E. coli* cells, under the aforementioned conditions, results in a reservoir of cells from which the plasmids are respectively isolated by techniques well known in the art.

The following examples further illustrate and detail the invention disclosed herein. Both an explanation of and the actual procedures for constructing the invention are described where appropriate.

EXAMPLE 1

Construction of Plasmid pOW10

A. Construction of the ~0.38 kb EcoRI-SfaNI Fragment of Plasmid pMS480

1. Isolation of Plasmid pMS480

The bacterium *E. coli* K12 JA221/pMS480 (NRRL B-15258) was cultured in TY broth (1% tryptone, 0.5% yeast extract, 0.5% sodium chloride, pH 7) with 100 μg./ml. of antibiotic ampicillin according to conventional-microbiological procedures. After 18 hours incubation, about 0.5 ml. of the culture was transferred to a 1.5 ml. Eppendorf tube and centrifuged for about 15 seconds. Unless otherwise indicated, all the manipulations were done at ambient temperature. The resultant supernatant was carefully removed with a fine-tip aspirator and the cell pellet was suspended in about 100 μl. of freshly prepared lysozyme solution which contained 2 mg./ml. lysozyme, 50 mM glucose, 10 mM EDTA (ethylene diaminetetracetate) and 25 mM Tris-HCl (pH 8). After incubation at 0° C. for 30 minutes, about 200 μl. of alkaline SDS (sodium dodecyl sulfate) solution (.2N NaOH, 1% SDS) were added and then the tube was gently vortexed and maintained at 0° C. for 5 minutes. Next, about 150 μl. of 3M sodium acetate (prepared by dissolving 3 moles of sodium acetate in a minimum of water, adjusting the pH to 4.8 with glacial acetic acid and then adjusting the volume-to 1 l.) were added a DNA clot formed after the contents of the tube were mixed gently for a few seconds by inversion.

The tube was maintained at 0° C. for 60 minutes and then centrifuged for 5 minutes to yield an almost clear supernatant. About 0.4 ml. of the supernatant was transferred to a second centrifuge tube to which 1 ml. of cold ethanol was added. After the tube was held at −20° C. for 30 minutes, the resultant precipitate was collected by centrifugation (2 minutes) and the supernatant was removed by aspiration. The thus collected pellet was dissolved in 200 μl. of 0.1M sodium acetate/0.05 M Tris-HCl (pH 8) and was reprecipitated by the addition of 2 volumes of cold ethanol. After 10 minutes at −20° C., the precipitate was collected by centrifugation and constituted the desired plasmid pMS480 DNA.

2. EcoRI-SfaNI Digestion of Plasmid pMS480

About 5 μl. (5 μg.) of plasmid pMS480 (isolated in Example A-1) in TE buffer (10 mM Tris-HCl, pH 8., 1 mM EDTA), 5 μl. DTT (100 mM Dithiothreitol), 5 μl. (1000 μg./ml.) BSA (bovine serum albumin), 25 μl. water, 5 μl. (5 New England Biolab units) EcoRI restriction enzyme* and 5 μl. 10X reaction mix** were incubated at 37° C. for about 1 hour. The reaction was terminated by incubation at 65° C. for 10 minutes. Next, the reaction mixture was cooled on ice and then about 1.1 μl. of 5 M NaCl, 4 μl. water and 5 μl. (5 New England Bio lab units) SfaNI restriction enzyme were added followed by a second incubation at 37° C. for 1 hour. The reaction was terminated by incubation at 65° C. for 10 minutes and then the reaction mixture was cooled on ice, extracted with each of phenol and chloroform:isoamyl alcohol (24:1) and then ethanol precipitated. The desired ~0.38 kb EcoRI-SfaNI restriction fragments were conventionally separated and isolated by agarose gel electrophoresis (Maniatis et al., 1982, Molecular Cloning, Cold Spring Harbor Laboratory, Cold Spring Harbor, N.Y.). The desired ~0.38 kb fragments were dissolved in about 30 μl. of water.

*Restriction and other enzymes can be obtained from the following sources:

New England Bio Labs., Inc.
32 Tozer Road
Beverly, Mass. 01915

Boehringer-Mannheim Biochemicals
7941 Castleway Drive
Indianapolis, Ind. 46250

**Reaction mix (10X) for EcoRI restriction enzyme was prepared with the following composition:
500 mM NaCl
1000 mM Tris-HCl, pH 7.2
50 mM MgCl₂

B. Construction of the ~4 kb EcoRI-NcoI Fragment of Plasmid pOW601

1. Isolation of Plasmid pOW601

Plasmid pOW601 is isolated from *E. coli* K12 JA221/pOW601 (NRRL B-15259). The strain was cultured and the plasmid was isolated in substantial accordance with the teaching of Example 1A-1.

2. EcoRI-NcoI Digestion of Plasmid pOW601

The desired digestion is carried out in substantial accordance with the teaching of Example 1A-2 except that plasmid pOW601, rather than plasmid pMS480, was used.

C. Construction of the DNA Fragment

wherein R is G and R¹ is C

The desired construction involves the synthesis and 5' phosphorylation of oligonucleotides T₁ and T₂ shown below:

T₁ 5' AGTGAGGTGGATGC 3'

T₂ 5' CATGGCATCCACCT 3'

Oligonucleotides T₁ and T₂ were used to construct the desired DNA fragment having an NcoI sticky terminus. The oligonucleotide synthesis was conventionally done by the modified phosphotriester method using fully protected deoxyribonucleotide building blocks.

Figure 3:
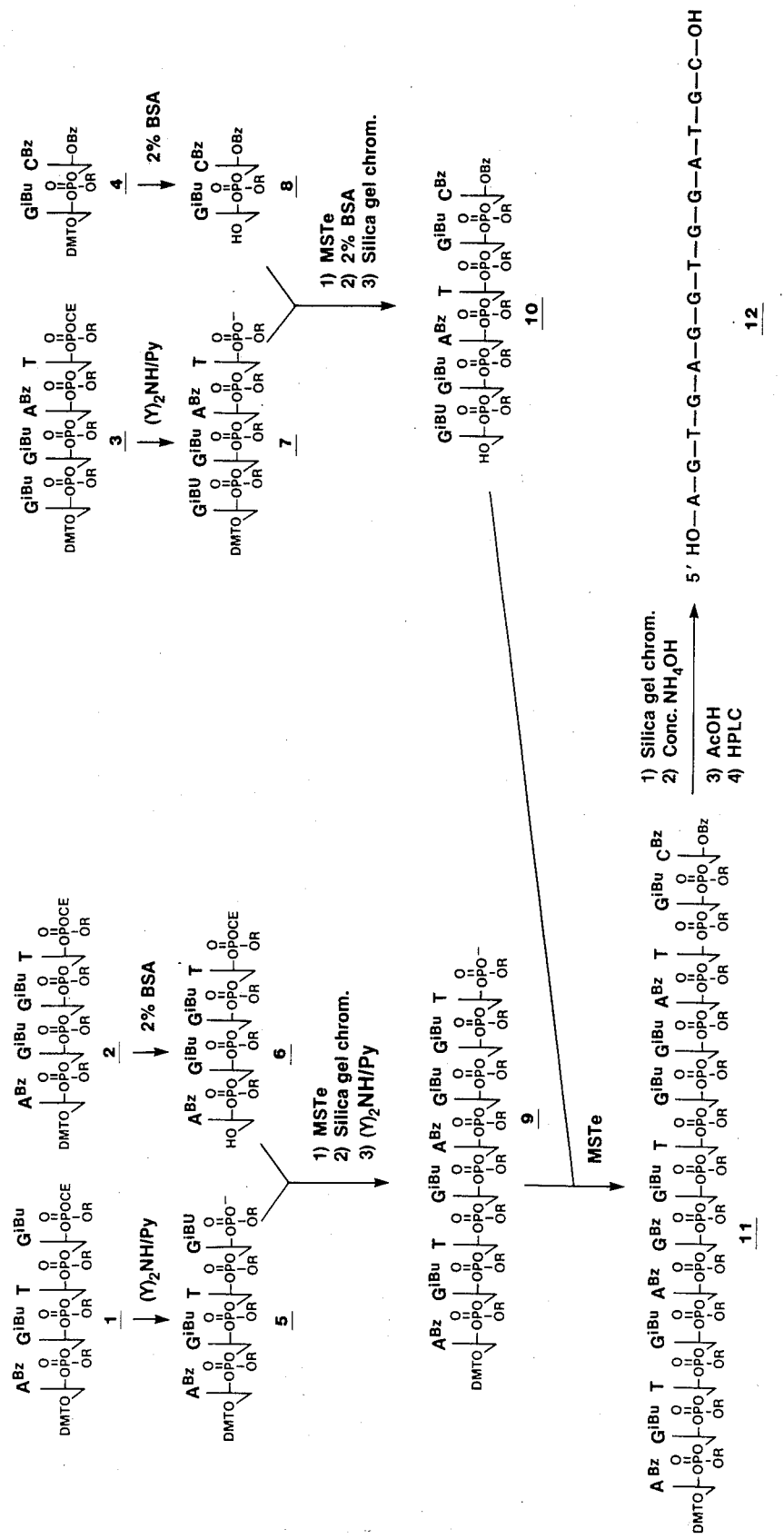

The above synthesis is typified by the following procedure for fragment T₁ as summarized in FIG. 3 of the accompanying drawings. Various nucleotide fragments that are used in the synthesis of T₁ are numerically designated in the figure. The abbreviations employed are as follows: MSTe, mesitylenesulfonyltetrazole; BSA, benzene sulfonic acid; TLC, thin layer chromatography; HPLC, high performance liquid chromatography; DMT, 4,4'-dimethoxytrityl; CE, 2-cyanoethyl; R, p-chlorophenyl; Bz, benzoyl; (Y)₂NH, diisopropylamine; iBu, isobutyryl; Py, pyridine; AcOH, acetic acid.

The fully protected deoxyribotetranucleotides 2 (312 mg., 0.15 mmol) and deoxyribodinucleotides 4 (50 mg., 0.017 mmol) are deblocked at the 5' hydroxyls by treatment with 2% BSA in 7:3 (v/v) chloroform/methanol (2 and 1 ml., respectively) for 10 minutes at 0° C. Reactions are stopped by addition of saturated aqueous ammonium bicarbonate (2 ml.), extracted with chloroform (25 ml.), and washed with water (2x, 10 ml.). The organic layers are dried (magnesium sulfate), concentrated to small volumes (about 5 ml.), and precipitated by addition of petroleum ether (35°-60° C. fraction). The colorless precipitates are collected by centrifugation and dried in a dessicator in vacuo to give 6 and 8, respectively, each homogeneous by silica gel tlc (Merck 60 F254, chloroform/methanol, 9:1).

Tetramers 1 and 3 (400 mg., 0.17 mmol; 100 mg., 0.043 mmol) are converted into their phosphodiesters (5 and 6) by treatment with diisopropylamine/pyridine (1:5, v/v, 2 ml.) for 30 minutes at ambient temperature. The reaction mixture was then precipitated with the addition of anhydrous ether (20 ml.). Reagents are removed by centrifugation and decanting the supernatant. The residues are dried by evaporation with anhydrous pyridine. Dimer 8 (0.04 mmol) and tetramer 7 are combined with MSTe (65 mg., 0.25 mmol) in anhydrous pyridine (1 ml.) and the reaction mixture left at ambient temperature for two hours. TLC analysis shows that 95% of the dimer 8 has been converted into hexamer product (visualized by detection of the DMT group by spraying with 10% aqueous sulfuric acid and heating at 100° C.). The reaction mixture is precipitated by addition of ether and the supernatant is decanted. The hexamer is deblocked at the 5' position with 2% BSA (8 ml.) as described above for dimer 4 and tetramer 2. The product (10) is purified on a silica gel column (Merck 60 H, 3.5×5 cm.) by step gradient elution with chloroform/methanol (98:2 to 95:5, v/v). Fractions containing product 10 are evaporated to dryness. Similarly, tetramer 5 is coupled to tetramer 6 and the fully protected product directly purified on silica gel. This latter compound is deblocked at the 3' end by diisopropylamine/pyridine as described above to give fragment 9.

Finally, octomer 9 and hexamer 10 are coupled in anhydrous pyridine (0.5 ml.) with MSTe (100 mg., 0.39 mmol) as the condensing agent. Upon completion (45 minutes, ambient temperature) the mixture is rotary evaporated and the residue chromatographed on silica gel. A portion of compound 11 (20 mg.) in pyridine (0.5 ml.) is completely deblocked by treatment with concentrated ammonium hydroxide (7 ml., 8 hours, 60° C.) and subsequent treatment in 80% acetic acid (15 minutes, ambient temperature). After evaporation of acetic acid, the solid residue is dissolved in distilled water (2 ml.) and extracted with ethyl ether (3x, 2 ml.). The aqueous phase is concentrated to dryness and redissolved in 50% pyridine/water. The product was purified by preparative thin layer chromatography on PolyethyleneimineCellulose (PEI/UV₂₅₄) plates (Narang S. A. et al., 1980, Methods in Enzymology 65:610) and then by HPLC on a reverse phase C-18 column (Waters). The sequence of 12 is confirmed by two-dimensional sequence analysis.

Next, oligonucleotide T₂ was constructed. This was done in substantial accordance with the above synthesis protocol for oligonucleotide T₁.

Ten microgram quantities of the resultant oligonucleotide T₁ and T₂ are quantitatively phosphorylated with [γ-³²P]-ATP (New England Nuclear) in the presence of T₄ polynucleotide kinase to give specific activities of approximately 1 Ci/mmol. Radiolabelled fragments are purified by 20% polyacrylamide/7M urea gel electrophoresis and sequences of the eluted fragments are verified by two-dimensional electrophoresis/homochromatography (Jay et al., 1974, Nucleic acids Res. 1:331) of partial snake venom digests. Fragments T₁ and T₂ are then conventionally annealed to form the desired DNA fragment.

D. Construction of Plasmid pOW10 by ligation of (1) the ~0.38 kb EcoRI-SfaNI Fragment of Plasmid pMS480; (2) the ~4 kb EcoRI-NcoI Fragment of Plasmid pOW601 and (3) the Synthetic DNA Fragment of Example 1C and Construction of *E. coli* K12 JA221-/pOW10

About 8 μl. (0.01 μg.) of the ~0.38 kb EcoRISfaNI fragment of plasmid pMS480, 8 μl. (0.10 μg.) of the ~4 kb EcoRI-NcoI fragment of plasmid pOW601, 10 μl. (0.7 μg.) of the DNA fragment of Example 1C, 10 μl. water, 4 μl. (10 mM)ATP, 2.5 μl. (100 mM) dithiothreitol (DTT), 5 μl. ligation mix** and 2.5 μl. T4 DNA ligase* (~2 New England Bio Lab Units) were incubated at 16° C. for about 16 hours. The reaction was terminated by incubation at 65° C. for 10 minutes and then, after cooling on ice, the resultant ligated mixture was used to transform *E. coli* K12 JA221 (NRRL B-15211), in substantial accordance with the transformation procedure of Lederberg and Cohen, 1974, *J. Bacteriology* 119:1072, on TY plates containing 10 μg./ml. of antibiotic tetracycline. The resultant transformants were conventionally cultured and used for subsequent production and isolation of plasmid pOW10 in substantial accordance with the procedure of Example 1A. A restriction site map of plasmid pOW10 is shown in FIG. 1 of the accompanying drawings.

*T4 DNA ligase can be obtained from the following source:
New England Bio Labs., Inc.
32 Tozer Rd.
Beverly, Mass. 01915
Ligation mix was prepared with the following composition:
500 mM Tris-HCl, pH 7.6
100 mM MgCl₂

EXAMPLE 2

Construction of Plasmids pOW525 and pOW526 and *E. coli* K12 JA221/pOW525 and *E. coli* K12 JA221/pOW526

A. Isolation of Plasmid pHI-16

1. Culture of *Bacillus subtilis* MI112/pHI-16

A vegetative culture of *Bacillus subtilis* MI112/pHI-16 (NRRL B-12597) was conventionally prepared by plating on PAB agar (PAB* [Penassay broth] containing agar at 15 g./l. and chloramphenicol at 10 μg./ml.). After the inoculated plate was incubated at 37° C. for about 18 hours, a single colony was selected and used inoculating 500 ml. of sterilized PAB medium with 10 μg./ml. chloramphenicol. The resultant inoculated broth was incubated at 37° C. for about 18 hours afterwhich the resultant *Bacillus subtilis* MII12/pHI-16 cells were ready for harvest and subsequent isolation of plasmid DNA.

*PAB can be obtained from Difco Laboratories, Detroit Mich.

2. Plasmid Isolation

About 10 g. (wet wgt) of *Bacillus subtilis* MI112/pHI-16 cells were first harvested by centrifugation (10 minutes, 4° C., 10,000 rpm), then washed in about 50 ml. TES (10 mM Tris (pH 8), 10 mM NaCl, 1 mM EDTA) and finally collected again by centrifugation. About 20 ml. TE buffer with 25% sucrose were added to the pellet followed by about 10 mg. of lysozyme in 250 μl. water. The mixture was incubated at 37° C. for about 30 minutes followed by the addition of about 100 units of RNase. The resultant mixture was again incubated at 37° C. for 30 minutes and then, upon being made 1% and 1M with respect to SDS (sodium dodecyl sulfate) and sodium chloride respectively, the mixture was cooled in an ice bath for about 3 hours. After the lysate was centrifuged (30 minutes, 4° C., 19,000 rpm), the supernatent was adjusted to 31.8 ml. with TE, and then 28.7 g. of cesium chloride and 0.4 ml. (10 mg./ml.) of ethidium bromide were added. A cesium chloride gradient was established by centrifuging at 49,500 rpm 16 hours. The plasmid band was collected and centrifuged at 55,000 rpm for 16 hours, then collected again, extracted thrice with equal volumes of isoamyl alcohol, dialyzed against dilute TE, ethanol precipitated, and resuspended in 400 μl of TE. The resultant plasmid pHI-16 DNA was stored at 4° C. for future use.

The kanamycin resistance gene is contained within the ~0.74 kb HpaII fragment of plasmid pHI-16. Therefore, treatment with HpaII restriction enzyme followed by ligation results in a ~3.9 kb plasmid, designated herein as pHI-18, which lacks the kanamycin resistance gene. A detailed procedure for constructing plasmid pHI-18 is described below.

B. Construction of Plasmid pHI-18

1. Partial HpaII Digestion of Plasmid pHI-16

About 5 μl. (2.5 μg.) of plasmid pHI-16 DNA, 1 μl. (2 mg./ml.) BSA, 37 μl. water, 2 μl. of HpaII (containing 2 New England Bio Labs units) restriction enzyme, and 5 μl. reaction mix* were incubated at 37° C. for 1 hour. After the reaction was terminated by heating at 65° C. for 10 minutes, the DNA was precipitated by adding 2 volumes of 95% ethanol. The resultant DNA precipitate was washed in 70% ethanol, dried in vacuo, suspended in 5 μl. of TE buffer, and stored at 4° C. for future use.

*Reaction mix for HpaII restriction enzyme was prepared with the following composition.
60 mM KCl
100 mM Tris-HCl, pH 7.4
100 mM MgCl₂
10 m Dithiothreitol 2. Ligation of Plasmid pHI-16 HpaII Digest About 5 μl of plasmid pHI-16 HpaII digest (prepared in Example 3B-1), 2 μl T4 DNA ligase, and 43 μl. ligation mix* were incubated at about 16° C. for about 18 hours. The reaction was terminated by the addition of about 5 μl of 3M sodium acetate and 150 μl. of 95% ethanol. The desired DNA precipitate was washed in 70% ethanol, dried in vacuo, suspended in 10 μl. of TE buffer, and stored at 4° C. for future use.

Ligation mix was prepared with the following composition.
66 mM Tris-HCl, pH 7.8
10 mM Dithiothreitol
6.6 mM MgCl₂
4 mM ATP C. Construction of *Bacillus subtilis* MI112/pHI-18

*Bacillus subtilis* MI112 can be obtained by conventionally culturing *B. subtilis* MI112/pHI-16 (NRRL B-12597) in the absence of chloramphenicol. The *B. subtilis* MI112/pHI-16 cells spontaneously lose the pHI-16 plasmid under the aforementioned culture conditions thus generating the desired chloramphenicol sensitive *B. subtilis* MI112 strain. Those skilled in the art will recognize and understand that sensitivity to chloramphenicol can be employed for testing and insuring that only *B. subtilis* MI112 cells that lack the plasmid are selected and used in the Bacillus transformation procedures herein disclosed.

About 50 ml. of sterile PAB was inoculated with *Bacillus subtilis* MI112 and incubated at 37° C. until a cell density of $2 \times 10^8$ cells/ml. was reached. The cells were then protoplasted, using sterile technique, by pelleting and then resuspending the cells in about 5 ml. of SMMP (equal volumes of each of 4x PAB and a solution comprising 1.0M sucrose, 0.04M maleic acid, and 0.04M MgCl₂, pH adjusted to 6.5 with NaOH). Next, about 250 μl. of lysozyme (20 mg./ml. in SMM [0.5M sucrose, 0.02M maleic acid, and 0.02M MgCl₂, pH adjusted to 6.5 with NaOH]) were added using filter sterilization. The cells were incubated with gentle shaking at 37° C. for about 2 hours. The resultant protoplasts were pelleted, washed with 5 ml. SMMP, and then resuspended in 5 ml. SMMP. Following centrifugation (25° C., 12 minutes, 2,600 rpm), about 0.1 ml. of the protoplasts were transformed by adding about 20 μl. of a 1:1 mixture comprising plasmid pHI-18 DNA and 2X SMM. About 1.5 ml. of PEG solution (40 g. PEG 6000 [polyethyleneglycol], 50 ml. 2X SMM, and water to 100 ml.) were then immediately added and, after about 2 minutes, 5 ml. of SMMP were also added. Next, the protoplasts were pelleted, suspended in 1 ml. of SMMP, and incubated at 30° C. with gentle shaking for about 2 hours. Aliquots of the thus prepared suspension were plated on chloramphenicol containing DM3 regeneration medium which per liter had the following composition.

91 g. D-mannitol in 555 ml. deionized water containing 12 g. agar
10% Casamino acids 50 ml.
10% Yeast extract 50 ml.
20% Glucose 25 ml.
5% Dipotassium phosphate 100 ml.
1M MgCl₂ 20 ml.
10% Gelatin
10 mg Chloramphenicol The D-mannitol, casamino acids and yeast extract were autoclaved together. The gelatin was added immediately after autoclaving and the remaining ingredients were added after the mixture had cooled. The medium had a final chloramphenicol concentration of 10 μg./ml.

The resultant chloramphenicol resistant colonies were tested for kanamycin sensitivity. A chloramphenicol resistan and kanamycin sensitive colony was selected as the desired *Bacillus subtilis* MI112/pHI-18 strain. The strain was cultured and the identity further confirmed by conventional restriction enzyme and agarose gel electrophoretic analysis (Maniatis et al., 1982), of the constitutive plasmid.

D EcoRI Digestion of Plasmids pHI-18 and pOW10

About 4 μl (3 μg.) of pHI-18, 1 μl. (1 μg.) of pOW10, 5 μl. water, 1 μl. 10X EcoRI buffer and 1.5 μl. (containing 5 New England Bio Lab units) EcoRI restriction enzyme were incubated at 37° C. for 1.5 hours. After the reaction was terminated by incubation at 65° C. for 10 minutes, the EcoRI-digested DNA was cooled on ice, ethanol precipitated and then dissolved in 30 μl of water.

E. Ligation of the Plasmid pHI-18 and pOW10 EcoRI Digests and Construction of *E. coli* K12 JA221/pOW525 and *E. coli* K12 JA221/pOW526

About 30 μl of the pHI-18 and pOW10 EcoRI digests, 4 μl. (100 mM) 10X Dithiothreitol, 4 μl. (10 mM) ATP, 4 μl. 10X ligase buffer and 1 μl. (containing 3 New England Bio Lab units) T4 DNA ligase were incubated at 16° C. for about 4 hours. The reaction was terminated by incubation at 65° C. for 10 minutes and then, after cooling on ice, the resultant ligated DNA was used to transform *E. coli* K12 JA221 (NRRL B-15211), in substantial accordance with the transformation procedure of Lederberg and Cohen (1974), on TY plates containing 10 μg./ml. of tetracycline. The resultant transformants were conventionally cultured and used for subsequent production and isolation of plasmids pOW525 and pOW526 in substantial accordance with the procedure of Example 1A. Plasmids pOW525 and pOW526 can be conventionally identified and distinguished by restriction enzyme and agarose gel electrophoretic analysis (Maniatis et al., 1982). A restriction site map of each of plasmids pOW525 and pOW526 is presented in FIG. 1 of the accompanying drawings.

EXAMPLE 3

Construction of *Bacillus subtilis* MI112/pOW525 and *B. subtilis* MI112/pOW526

The desired constructions were made in substantial accordance with the procedure of Example 2C except that plasmids pOW525 and pOW526, rather than plasmid pHI-18, were used. The resultant *Bacillus subtilis* MI112/pOW525 and *B. subtilis* MI112/pOW526 chloramphenicol-resistant and kanamycin-sensitive transformant colonies are isolated, according to known procedures, and then conventionally identified by restriction enzyme and agarose gel electrophoretic analysis of the constitutive plasmids. The thus constructed transformants, useful for the subsequent production and isolation of plasmids pOW525 and pOW526, produce preproinsulin intracellularly and also secrete proinsulin into the culture medium. This was determined by in vitro assay of both cell lysates and the culture medium.

EXAMPLE 4

Construction of Plasmids pOW527 and pOW528 and *E. coli* K12 JA221/pOW527 and *E. coli* K12 JA221/pOW528

The desired constructions were made in substantial accordance with the teaching of Example 2 except that plasmid pBS1, rather than plasmid pHI-18, was used. Plasmid pBS1 is constructed as outlined below.

A. Isolation of Plasmid pEL103

1. Culture of *Streptomyces granuloruber* No. A39912.13/pEL103

A vegetative inoculum of *Streptomyces granuloruber* No. A39912.13/pEL103 (NRRL 12549) was conventionally prepared by growing the strain under submerged aerobic conditions in 50 ml. of sterilized trypticase soy broth* at 35 g./l. in deionized water.

The trypticase soy broth inoculum was incubated for 48 hours at a temperature of 30° C. After incubation, about 10 ml. of the inoculum was transferred to 500 ml. of the sterilized broth and was incubated for about 20 hours at 30° C. The pH was not adjusted. After incubation, the *Streptomyces granuloruber* No. A39912.13/pEL103 cells were ready for harvest and subsequent isolation of plasmid DNA.

*Trypticase soy broth is obtained from BBL Division, Becton-Dickinson & Company, Cockeysville, Md. 21030.

2. Plasmid Isolation

About 12 g. (wet wgt) of *Streptomyces granuloruber* No. A39912.13/pEL103 cells were centrifuged (10 minutes, 4° C., 10,000 rpm), washed in 10% glycerol, and then harvested by recentrifugation under the aforementioned conditions. About 50 ml. of TES buffer (0.01M Tris(hydroxymethyl)aminoethane [Tris], 0.001M EDTA, 34% sucrose, pH 8) were added to the cells followed by about 0.25 g. of lysozyme in 10 ml. of 0.25M EDTA. After the mixture was incubated at 37° C. for about 15 minutes, about 0.5 ml. of 10% Triton X-100 in TE buffer (0.01M Tris, 0.001M EDTA, pH 8) was added. The resultant mixture was then incubated at 65° C. for about 15 minutes. After the lysate was centrifuged (45 minutes, 4° C., 18,000 rpm), the supernatant was extracted four times with isoamyl alcohol and once with a chloroformisoamyl alcohol solution (24:1). Next, 0.1 volume of 3M sodium acetate was added to the aqueous phase followed by 3 volumes of cold (−20° C.) 95% ethanol. The ethanol precipitation was rapidly performed in a dry ice-ethanol bath and the DNA precipitate was collected by centrifugation (15 minutes, 4° C., 10,000 rpm). The precipitate was vacuum dried and then resuspended in 1.1 ml. of STE buffer (0.01M Tris, 0.001M EDTA, 0.01M sodium chloride). Centrifugation (40 hours, 15° C., 35,000 rpm) using cesium chloride gradients, with ethidium bromide, was carried out to purify the plasmid DNA. Following centrifugation, the desired plasmid pEL103 DNA band was removed and the ethidium bromide extracted by conventional procedures. After precipitation of the DNA in 3 volumes of ethanol, the thus isolated plasmid pEL103 DNA was dissolved in 1 ml. of 10 fold diluted TE buffer and was then stored at −20° C.

B. Construction of Plasmid pLR2

1. HindIII Digestion of Plasmid pIJ6

About 20 μl (20 μg.) of plasmid pIJ6 DNA, disclosed in Thompson et al., 1980, Nature 286:525, 5 μl BSA (Bovine Serum albumin, 1 mg./ml.), 19 μl. water, 1 μl. of HindIII (containing 3 New England Bio Labs units) restriction enzyme, and 5 μl. reaction mix* were incubated at 37° C. for 2 hours. The reaction was terminated by the addition of about 50 μl. of 4M ammonium acetate and 200 μl. of 95% ethanol. The resultant DNA precipitate was washed twice in 70% ethanol, dried in vacuo, suspended in 20 μl. of TE buffer, and stored at −20° C.
Reaction mix for HindIII restriction enzyme was prepared with the following composition.
600 mM NaCl
100 mM Tris-HCl, pH7.9
70 mM MgCl₂
10 mM Dithiothreitol 2. HindIII Digestion of Plasmid pBR322

About 8 μl (4 μg.) of plasmid pBR322 DNA*, 5 μl reaction mix, 5 μl BSA (1 mg./ml.), 31 μl. and 1 μl. of HindIII restriction enzyme were incubated at 37° C. for 2 hours. After the reaction was terminated by incubating at 60° C. for 10 minutes, about 50 μl. of 4M ammonium acetate and 200 μl. of 95% ethanol were added. The resultant DNA precipitate was washed twice in 70% ethanol, dried in vacuo, and suspended in 45 μl. of water.
* Plasmid pBR322 can be obtained from Boehringer-Mannheim Biochemicals the address of which is disclosed in Example 1A-2.

3. Ligation of HindIII Digested Plasmids pIJ6 and pBR322

About 20 μl of HindIII treated plasmid pIJ6, 20 μl of HindIII treated plasmid pBR322, 5 μl BSA (1 mg./ml.), 1 μl. of T4 DNA ligase, and 5 μl. ligation mix* were incubated at 16° C. for 4 hours. The reaction was terminated by the addition of about 50 μl. 4M ammonium acetate and 200 μl of 95% ethanol. The resultant DNA precipitate was washed twice in 70% ethanol, dried in vacuo, and suspended in TE buffer. The suspended DNA constituted the desired plasmid pLR2.
*Ligation mix was prepared with the following composition.
500 mM Tris-HCl, pH 7.8
200 mM Dithiothreitol
100 mM MgCl₂
10 mM ATP C. Construction of E. coli K12 HB101/pLR2

About 10 ml. of E. coli K12 HB101 cells (Bolivar et al., 1977, Gene 2:75–93) were pelleted by centrifugation and then suspended in about 10 ml. of 0.01M sodium chloride. Next, the cells were pelleted again, resuspended in about 10 ml. of 0.03M calcium chloride, incubated on ice for 20 minutes, pelleted a third time, and finally, resuspended in 1.25 ml. of 0.03M calcium chloride. The resultant cell suspension was competent for subsequent transformation.

Plasmid pLR2 in TE buffer was ethanol precipitated, suspended in 150 μl of 30 mM calcium chloride solution, and gently mixed in a test tube with about 200 μl. of competent E. coli K12 HB101 cells. The resultant mixture was incubated on ice for about 45 minutes and then at 42° C. for about 1 minute. Next, about 3 ml. of L-broth (Bertani, 1951, J. Bacteriology 62:293) containing 50 μg./ml. of ampicillin was added. The mixture was incubated with shaking at 37° C. for 1 hour and then plated on L-agar (Miller, 1972, Experiments in Molecular Genetics, Cold Spring Harbor Labs, Cold Spring Harbor, N.Y.) containing ampicillin. Surviving colonies were selected and tested for the expected phenotype (Amp$^R$, Tet$^S$), and constituted the desired E. coli K12 HB101/pLR2 transformants.

D. Construction of Plasmids pEL107 and pEL105

1. BamHI Digestion of Plasmid pLR2 and Isolation of the ∼1.6 kb Thiostrepton Resistance-Conferring Fragment About 50 μg. of plasmid pLR2 DNA, 10 μl. reaction mix, 10 μl. BSA (1 mg./ml.), 29 μl. water, and 1 μl. (4 units/μl.) of BamHI restriction enzyme were incubated at 37° C. for 2 hours. After adding an equal volume of 4M ammonium acetate and 2.5 volumes of 95% ethanol, the mixture was cooled at −20° C. for about 18 hours to precipitate the DNA. The DNA precipitate was collected by centrifugation and then suspended in about 50 μl. of TE buffer. The desired ∼1.6 kb BamHI restriction fragment was isolated conventionally from the DNA suspension by agarose gel electrophoresis (Maniatis et al. 1982). Following isolation, the fragment was resuspended in about 20 μl. of TE buffer for subsequent ligation.

2. Partial BamHI Digestion of Plasmid pEL103

About 20 μg. of plasmid pEL103 DNA, 10 μl. reaction mix, 10 μl. BSA (1 mg./ml.), 39 μl. water, and 1 μl. of BamHI restriction enzyme (prepared by diluting 2 μl. of enzyme in 8 μl. of water) were incubated at ambient temperature for about 15 minutes. After adding an equal volume of 4M ammonium acetate and 2 volumes of 95% ethanol, the mixture was cooled at −20° C. for about 18 hours to precipitate the DNA. The DNA precipitate was collected by centrifugation, rinsed in 70% ethanol, dried in vacuo, and then suspended in about 50 μl. of TE buffer.

3. Ligation

A mixture of about 20 μg. of the partially digested plasmid pEL103 DNA, 10 μg. of the ∼1.6 kb BamHI restriction fragment of plasmid pLR2, 5 μl. ligation mix, 5 μl. BSA (1 mg./ml.), 10 μl. water, and 1 μl. T4 DNA ligase were incubated at about 16° C. for about 4 hours. After adding 40 μl. of 4M ammonium acetate and 200 μl. of cold ethanol, the mixture was cooled to −20° C. for about 18 hours to precipitate the DNA. The DNA precipitate was collected by centrifugation, washed with 70% ethanol, collected again, and then suspended in 50 μl. of medium P (Hopwood and Wright 1978,Molecular and General Genetics 162:307) for subsequent transformation.

Figure 4:
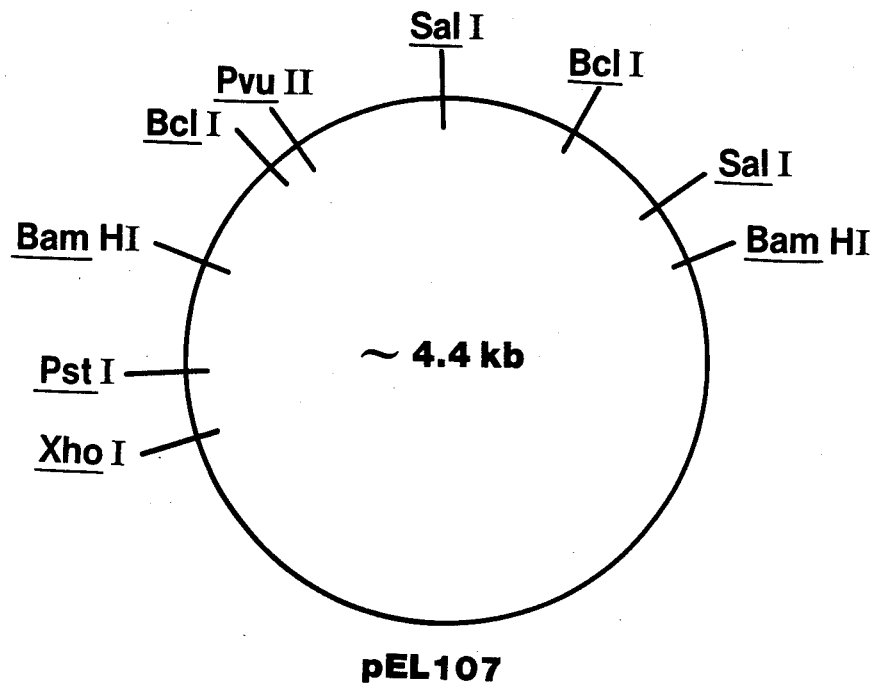
Figure 4:
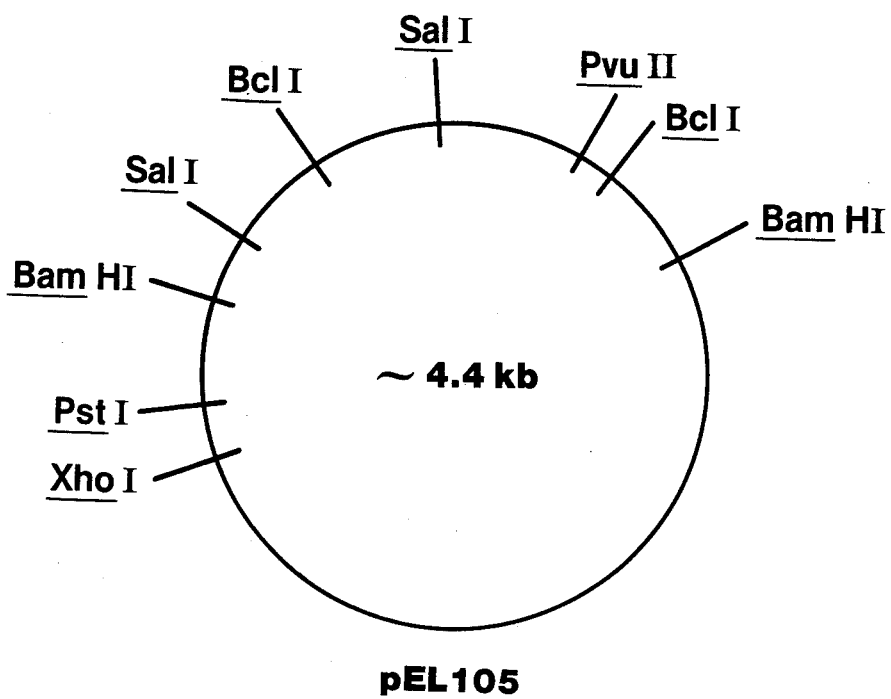

Recombinant plasmids of various types result depending upon which of the possible pEL103 restriction fragments becomes ligated to the ∼1.6 kb BamHI thiostrepton resistance-conferring fragment. Ligation to the ∼2.8 kb BamHI restriction fragment of plasmid pEL103 results in the desired ∼4.4 kb plasmids pEL107 and pEL105. Recombinant plasmids of two orientations result because the ∼1.6 kb BamHI resistance-conferring fragment can be oriented in either direction. A restriction site and functional map of each of plasmids pEL107 and pEL105 is presented in FIG. 4 of the accompanying drawings.

Construction of Streptomyces ambofaciens/pEL107 and S. ambofaciens/pEL105

Using about 20 μg. of the DNA from Example 4D-3 and 1X10⁸ protoplasts (prepared according to Baltz, 1978, J. of General Microbiology 107:93) of Streptomyces ambofaciens, a strain deposited and made part of the permanent stock culture collection of the Northern Regional Research Laboratory, Peoria, Ill., from which it is available to the public under the accession number NRRL 2420, the desired constructions were made in substantial accordance with the teaching of International Publication (of International Patent Application No. PCT/GB79/00095) No. WO79/01169, Example 2. The desired transformants were selected for thiostrepton resistance by overlaying the regenerating protoplasts with modified R2 medium (Baltz, 1978, J. of General Microbiology 107:93) top agar containing sufficient thiostrepton to bring the final plate concentration to 50 μg./ml. The resultant Streptomyces ambofaciens/- pEL107 and *S. ambofaciens*/pEL105 thiostrepton resistant colonies were isolated according to known procedures, cultured, and then identified by restriction enzyme and gel electrophoretic analysis (Maniatis et al., 1982), of the constitutive plasmids.

Accordingly, vegetative inocula (10 ml.) of different isolated colonies are conventionally prepared by inoculating trypticase soy broth containing sufficient thiostrepton to bring the final concentration to 50 μg./ml. Several inocula are prepared and the following procedure performed until all the desired transformant types and constitutive plasmids are isolated. Thus, after cells are incubated at 30° C. until fully grown, 6 ml. of the cell-containing broth are centrifuged. The resultant pellet is washed in TE buffer, pelleted again, and then suspended in 400 μl. 50 mM Tris, pH 8.0. Next, about 80 μl. of 0.25M EDTA, 20 μl. RNase, and 100 μl. (10 mg./ml. in TE) lysozyme are added. After the mixture is incubated at 37° C. for about 15 minutes, about 10 μl. of 10% Triton X-100 and 150 μl. 5M NaCl are added followed by a final incubation at 60° C. for 15 minutes. The resultant lysate is centrifuged (15 minutes, 4° C., 15,000 rpm) and then the supernatant is conventionally extracted twice with phenol, once with a chloroform-isoamyl alcohol solution (24:1), and then ethanol precipitated. The identity of the constitutive plasmids and thus the transformants are determined conventionally by restriction enzyme and agarose gel electrophoretic analysis (Maniatis et al., 1982). Plasmid pEL105 was conventionally isolated for subsequent construction of plasmid pBS1.

F. Construction of Plasmids pBS1 and pBS3

1. Partial BamHI Digestion of Plasmid pEL105

About 10 μl. (5 μg.) of plasmid pEL105 (conventionally isolated from *Streptomyces ambofaciens*/-pEL105 [prepared in Example 4E]in substantial accordance with the teaching of Example 4A-1), 2 μl. BSA (1 mg./ml.), 29 μl. water, 1 μl. of BamHI (diluted 1:4 water) restriction enzyme, and 5 μl. reaction mix were incubated at 25° C. for 15 minutes. The reaction was terminated by the addition of about 50 μl. of 4M ammonium acetate and 300 μl. of 95% ethanol. After cooling at −20° C. for about 2 hours, the resultant DNA precipitate was collected by centrifugation, washed twice in 70% ethanol, dried in vacuo, and then suspended in about 10 μl. of TE buffer. Because plasmid pEL105 has two BamHI restriction sites, a mixture of different fragments results.

2. Bam Digestion of Plasmid pHI-18

About 5 μl. (5 μg.) of plasmid pHI-18, 2 μl. BSA (1 mg./ml.), 9 μl. water, 1 μl. of BamHI (4 units/-μl.) restriction enzyme, and 1.5 μl. reaction mix were incubated at 37° C. for about 2 hours. After adding an equal volume of 4M ammonium acetate and 2.5 volumes of 95% ethanol, the mixture was cooled at −20° C. for about 18 hours to precipitate the DNA. The DNA precipitate was collected by centrifugation, washed in 70% ethanol, and then suspended in about 10 μl. of TE buffer.

3. Ligation

About 5 μl. of BamHI-digested plasmid pHI-18, 8 μl. of plasmid pEL105 BamHI partial digest, 27 μl. water, 5 μl. (4 mM) ATP, 5 μl. ligation mix, and 2 μl. T4 DNA ligase were incubated at 16° C. for about 18 hours. The reaction was terminated by the addition of 50 μl. 4M ammonium acetate and 200 μl. of 95% ethanol. After incubation at −20° C. for about 2 hours, the desired plasmid pBS1 and pBS3 DNA precipitate was collected by centrifugation, washed in 70% ethanol, dried in vacuo, suspended in 10 μl. of TE buffer, and stored at 4° C. for future use.

Figure 5:
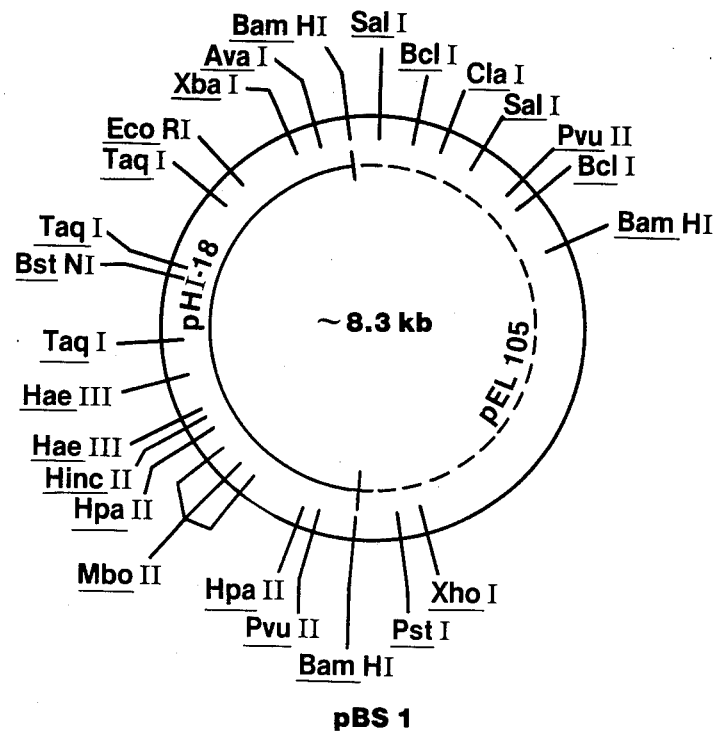
Figure 5:
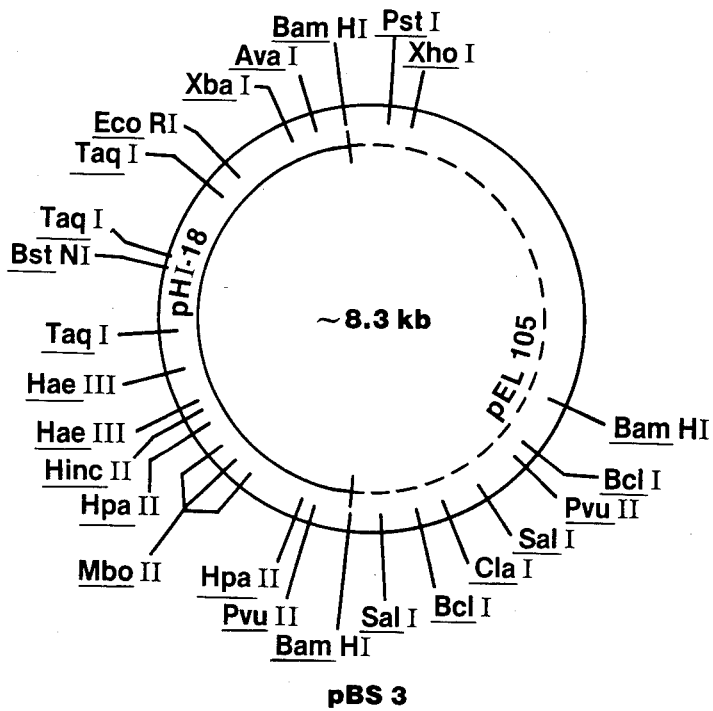

Since plasmid pEL105 has two BamHI restriction sites, a partial BamHI digest results in two ~4.4 kb BamHI fragments. Therefore, the insertional isomers of plasmids pBS1 and pBS3 are also produced by the above procedure. Recombinant plasmids of two orientations result because the BamHI restricted DNA can be ligated in either direction. A restriction site and functional map of each of plasmids pBS1 and pBS3 is presented in FIG. 5 of the accompanying drawings.

G. Construction of *Bacillus subtilis* MI112/pBS1 and *B. subtilis* MI112/pBS3

The desired constructions were made in substantial accordance with the procedure of Example 2C except that plasmids pBS1 and pBS3, rather than plasmid pHI-18, were used. The resultant *Bacillus subtilis* MI112/pBS1 and *B. subtilis* MI112/pBS3 chloramphenicol resistant and kanamycin sensitive transformant colonies were isolated according to known procedures, cultured and then conventionally identified by restriction enzyme and agarose gel electrophoretic analysis (Maniatis et al., 1982), of the constitutive plasmids. *Bacillus subtilis* MI112/pBS1 was selected and cultured for subsequent isolation of plasmid pBS1.

H. Final Construction of Plasmids pOW527 and pOW528 and *E. coli* K12 JA221/pOW527 and *E. coli* K12 JA221/pOW528

The desired plasmids pOW527 and pOW528 and transformants *E. coli* K12 JA221/pOW527 and *E. coli* K12 JA221/pOW528 were constructed in substantial accordance with the procedure of Example 2 except that plasmid pBS1, rather than plasmid pHI-18, was used. Recombinant plasmids of two orientations result because the EcoRI-restricted DNA can be ligated in either direction. A restriction site map of each of plasmids pOW527 and pOW528 is presented in FIG. 1 of the accompanying drawings.

EXAMPLE 5

Construction of *Bacillus subtilis* MI112/pOW527 and *B subtilis* MI112/pOW528

The desired constructions are made in substantial accordance with the teaching of Example 2C except that plasmids pOW527 and pOW528, rather than plasmid pHI-18, are used. The resultant *Bacillus subtilis* MI112/pOW527 and *B. subtilis* MI112/pOW528 chloramphenicol resistant and kanamycin sensitive transformant colonies are isolated, according to known procedures, and then conventionally identified by restriction enzyme and agarose gel electrophoretic analysis (Maniatis et al., 1982), of the constitutive plasmids. The thus constructed transformants, useful for the subsequent production and isolation of plasmids pOW527 and pOW528, produce pre-proinsulin intracellularly and also secrete proinsulin into the culture medium. This was determined by in vitro assay of both cell lysates and the culture medium.

EXAMPLE 6

Construction of Plasmid pOW303 and *E. coli* K12 BE904/ pOW303

A. NcoI Digestion of Plasmid pOW10

About 2 μl. (2 μg.) of plasmid pOW10 (prepared in Example 1D), in TE buffer, 2.5 μl. (100 mM) DTT, 0.5 μl. (1000 μg./ml.) BSA, 17 μl. water, 1 μl. (containing 4 New England Bio Lab Units) NcoI restriction enzyme and 2.5 µl. 10X reaction mix* were incubated at 37° C. for 1.5 hours. After the reaction was terminated by incubation at 65° C. for 10 minutes, the digested DNA was ethanol precipitated and then dissolved in 34.5 µl. of water.

*Reaction mix for NcoI restriction enzyme was prepared with the following composition.
1500 mM NaCl
60 mM Tris-HCl, pH 7.
60 mM MgCl$_2$

B. BamHI Digestion of Plasmid pMC1403

The desired digestion was carried out in substantial accordance with the teaching of Example 6A except that plasmid pMC1403 and BamHI restriction enzyme and reaction mix, rather than plasmid pOW10 and NcoI restriction enzyme and reaction mix, were used. Plasmid pMC1403 was isolated from *E. coli* K12 BE904/pMC1403 (NRRL B-15213) in substantial accordance with the teaching of Example 1A-1. The digested DNA was ethanol precipitated and then dissolved in 34.5 µl. of water.

C. Klenow Fill-in of NcoI-Digested Plasmid pOW10 and BamHI-Digested Plasmid pMC1403

The NcoI and BamHI digests of Examples 6A and 6B were combined (69 µl.) and then incubated with 4 µl. each of dATP, dGTP, dCTP and TTP, 5 µl. (containing 10 units of DNA polymerase I large (Klenow) fragment* and 10 µl. of 10X Klenow buffer (0.5M Tris-HCl, pH 7.2, 0.1M MgSO$_4$, 1 mM DTT) at 16° C. for 30 minutes. After the reaction was terminated by incubation at 65° C. for 10 minutes, the DNA was ethanol precipitated, extracted once with phenol and twice with chloroform:isoamyl alcohol (24:1) and then ethanol precipitated again. The Klenow filled-in DNA was dissolved in 20 µl. of water for subsequent EcoRI digestion.

*The Klenow fragment of DNA polymerase I can be obtained from the following source.
Boehringer-Mannheim Biochemicals
7941 Castleway Drive
Indianapolis, Ind. 46250

D. EcoRI Digestion of the Klenow Filled-In NcoI and BamHI Fragments

About 20 µl. (4 µg.) of the Klenow filledin DNA, 5 µl. (100 mM) DTT, 5 µl. (1000 mg./ml.) BSA, 2 µl. (containing 10 New England Bio Lab Units) EcoRI restriction enzyme and 5 µl. (10X) reaction mix were incubated at 37° C. for 1 hour and then at 65° C. for 10 minutes. The resultant EcoRI-digested DNA was ethanol precipitated and then dissolved in 30 µl. of water.

E. Ligation of the EcoRI-Digested Klenow Filled-In NcoI and BamHI Fragments and Construction of *E coli* K12 BE904/pOW303

About 30 µl. of the EcoRI-digested Klenow filled-in fragments, 4 µl. (100 mM) DTT, 4 µl. (100 mM) ATP, 4 µl. 10X ligase buffer and 1 µl. (containing 10 New England Bio Lab Units) T4 DNA ligase were incubated at 16° C. for about 16 hours and then at 65° C. for 10 minutes. After cooling on ice about 15 µl. of the resultant ligated DNA, designated herein as plasmid pOW303, was used to transform *E. coli* K12 BE904 (NRRL B-15212). This was done in substantial accordance with the procedure of Example 1D except that plasmid pOW303, rather than plasmid pOW10, was used and 80 µg./ml. of ampicillin was used instead of tetracycline. In addition, the TY plates contained 40 µg./ml. of 5-bromo-4-chloro-3-indolyl-βD-galactoside (x-gal) so that color could be used as a convenient assay of β-galactosidase activity. The resultant blue and ampicillin-resistant transformants constituted the desired *E. coli* K12 BE904/pOW303. The transformants were cultured, using conventional microbiological techniques, and were used for subsequent production and isolation of plasmid pOW303 in substantial accordance with the procedure of Example 1A-1. A restriction site map of plasmid pOW303 is presented in FIG. 2 of the accompanying drawings.

EXAMPLE 7

Construction of Plasmids pOW523 and pOW524 and *E. coli* K12 BE904/pOW523 and *E. coli* K12 BE904/pOW524

The desired constructions were made in substantial accordance with the teaching of Examples 2D and 2E except that plasmid pOW303, rather than plasmid pOW10, and 80 µg./ml. of ampicillin was used instead of tetracycline. In addition, the TY plates contained 40 µg./ml. of x-gal so that color could be used as a convenient assay of β-galactosidase activity. Recombinant plasmids of two orientations result because the EcoRI-restricted DNA can be ligated in either direction. A restriction site map of each of plasmids POW523 and pOW524 is presented in FIG. 2 of the accompanying drawings.

EXAMPLE 8

Construction of *Bacillus subtilis* MI112/pOW523 and *B. subtilis* MI112/pOW524

The desired constructions were made in substantial accordance with the teaching of Example 2C except that plasmids pOW523 and pOW524, rather than plasmid pHI-18, were used. In addition, the regeneration medium was modified so as to contain 40 µg./ml. of x-gal so that color would be used as a convenience assay of β-galactosidase activity. The resultant *Bacillus subtilis* MI112/pOW523 and *B. subtilis* MI112/pOW524 chloramphenicol-resistant and kanomycin-sensitive transformant colonies were isolated according to known procedures. The transformants produced dark blue colonies on x-gal-containing plates indicating that the gene that encoded the β-galactosidase activity was in the correct translational reading phase for direct expression. This was further confirmed by in vitro assay, which showed the presence of β-galactosidase activity in the transformants, and also by structural analysis of the plasmids. The desired *B. subtilis*MI112/pOW523 and *B. substilis* MI112/pOW524 transformants were cultured and then conventionally identified by restriction enzyme and agarose gel electrophoretic analysis (Maniatis et al., 1982), of the constitutive plasmids.

EXAMPLE 9

Construction of Plasmids pOW529 and pOW530 and *E. coli* K12 BE904/pOW529 and *E. coli* K12 BE904/pOW530

The desired constructions are made in substantial accordance with the teaching of Examples 2D and 2E except that plasmids pOW303 and pBS1, rather than plasmid pOW10 and pHI-18, are used and 80 µg./ml. of ampicillin is used instead of tetracycline. In addition, the TY plates contain 40 µg./ml. of x-gal so that color can be used as a convenient assay of β-galactosidase activity. Recombinant plasmids of two orientations result because the EcoRI-restricted DNA can be ligated in either direction. A restriction site map of each of plasmids pOW529 and pOW530 is presented in FIG. 2 of the accompanying drawings.

EXAMPLE 10

Construction of *Bacillus subtilis* MI112/pOW529 and *B. subtilis* MI112/pOW530

The desired constructions are made in substantial accordance with the teaching of Example 8 except that plasmids pOW529 and pOW530, rather than plasmids pOW523 and pOW524, are used. The transformants produce dark blue colonies on x-gal containing plates indicating that the gene that encodes the β-galactosidase activity is in the correct translational reading phase for direct expression. This is further confirmed by in vitro assay, which shows the presence of β-galactosidase activity in the transformants, and also by structural analysis of the plasmids. The desired *B. substilis* MI112/pOW529 and *B. substilis* MI112/pOW530 transformants are cultured and then conventionally identified by restriction enzyme and agarose gel electrophoretic analysis (Maniatis et al., 1982), of the constitutive plasmids.

EXAMPLE 11

Construction of the DNA Fragment

wherein R is C and R¹ is G

The desired construction involves the synthesis and 5' phosphorylation of oligonucleotides T₃ and T₄ shown below.

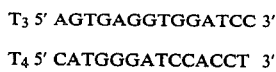

T₄ 5' CATGGGATCCACCT 3'

Oligonucleotides T₃ and T₄ were used to construct the desired DNA fragment having an NcoI sticky terminus adjacent to a BamHI restriction site. The oligonucleotide synthesis was conventionally done by the modified phosphotriester method using fully protected deoxyribonucleotide building blocks. The desired construction was made in substantial accordance with the teaching of Example 1C.

EXAMPLE 12

Construction of Plasmid pOW11 and *E. coli* K12 JA221/pOW11

The desired constructions are made in substantial accordance with the teaching of Example 1 except that the DNA fragment of Example 11, rather than the DNA fragment of Example 1C, is used. The restriction site map of plasmid pOW11 is the same, except for the aforementioned BamHI site, as that shown for plasmid pOW10 in FIG. 1 of the accompanying drawings.

EXAMPLE 13

Construction of Plasmids pOW531 and pOW532 and *E. coli*K12 JA221/pOW531 and *E. coli* K12 JA221/pOW532

The desired constructions are made in substantial accordance with the teaching of Example 2 except that plasmid pOW11, rather than plasmid pOW10, is used. The respective restriction site map of each of plasmids pOW531 and pOW532 is the same, except for the aforementioned additional BamHI site from the pOW11 fragment, as that shown for plasmids pOW525 and pOW526 in FIG. 1 of the accompanying drawings.

EXAMPLE 14

Construction of *Bacillus subtilis* MI112/pOW531 and *Bacillus subtilis* MI112/pOW532

The desired constructions are made in substantial accordance with the teaching of Example 3 except that plasmids pOW531 and pOW532, rather than plasmids pOW525 and pOW526, are used.

EXAMPLE 15

Construction of Plasmids pOW533 and pOW534 and *E. coli*JA221/pOW533 and *E. coli* K12 JA221/pOW534

The desired constructions are made in substantial accordance with the teaching of Example 4 except that plasmid pOW11, rather than plasmid pOW10, is used. The respective restriction site map of each of plasmids pOW533 and pOW534 is the same, except for the aforementioned additional BamHI site from the pOW11 fragment, as that shown for plasmids pOW527 and pOW528 in FIG. 1 of the accompanying drawings.

EXAMPLE 16

Construction of *Bacillus subtilis* MI112/pOW533 and *Bacillus subtilis* MI112/pOW534

The desired constructions are made in substantial accordance with the teaching of Example 5 except that plasmid pOW533 and pOW534, rather than plasmids pOW527 and pOW528, are used.

EXAMPLE 17

Construction of Plasmid pOW310 and *E. coli* K12 BE904/pOW310

The desired constructions are made in substantial accordance with the teaching of Example 6 except that plasmid pOW11, rather than plasmid pOW10, is used. The restriction site map of plasmid pOW310 is the same, except for the aforementioned additional BamHI site from the pOW11 fragment, as that shown for plasmid pOW303 in FIG. 2 of the accompanying drawings.

EXAMPLE 18

Construction of Plasmids pOW535 and pOW536 and *E. coli*K12 BE904/pOW535 and *E. coli* K12 BE904/pOW536

The desired constructions are made in substantial accordance with the teaching of Example 7 except that plasmid pOW310, rather than plasmid pOW303, is used. The restriction site map of each of plasmids pOW535 and pOW536 is the same, except for the aforementioned additional BamHI site from the pOW310 fragment, as that presented for plasmids pOW523 and pOW524 in FIG. 2 of the accompanying drawings.

EXAMPLE 19

Construction of *Bacillus subtilis* MI112/pOW535 and *Bacillus subtilis* MI112/pOW536

The desired constructions are made in substantial accordance with the teaching of Example 8 except that plasmids pOW535 and pOW536, rather than plasmids pOW523 and pOW524, are used.

EXAMPLE 20

Construction of Plasmids pOW537 and pOW538 and *E. coli* K12 BE904/pOW537 and *E. coli* K12 BE904/pOW538

The desired constructions are made in substantial accordance with the teaching of Example 9 except that plasmid pOW310, rather than plasmid pOW303, is used. The restriction site map of each of plasmids pOW537 and pOW538 is the same, except for the aforementioned additional BamHI site from the pOW310 fragment, as that presented for plasmids pOW529 and pOW530 in FIG. 2 of the accompanying drawings.

EXAMPLE 21

Construction of *Bacillus subtilis* MI112/pOW537 and *Bacillus subtilis* MI112/pOW538

The desired constructions are made in substantial accordance with the teaching of Example 10 except that plasmid pOW537 and pOW538, rather than plasmids pOW529 and pOW530, are used.

EXAMPLE 22

Construction of Plasmid pOW323/Z and *E. coli* K12 JA221/pOW323/Z

A. Isolation of Plasmid pOW440

The bacterium *Bacillus subtilis* MI112/pOW440 (NRRL B-15887) was cultured and plasmid pOW440 isolated in substantial accordance with the teaching of Example 2. The desired plasmid pOW440 was dissolved in TE buffer and stored at 0° C. for future use.

B. Sau3A Digestion of Plasmid pOW440 and Isolation of the ~518 bp (base pair) Fragment The desired digestion was carried out in substantial accordance with the teaching of Example 6A except that plasmid pOW440 and Sau3A restriction enzyme and reaction mix*, rather than plasmid pOW10 and NcoI restriction enzyme and reaction mix, were used. The desired ~518 bp fragments were conventionally separated and isolated by agarose gel electrophoresis (Maniatis et al., 1982), dissolved in 20 μl. of TE and stored at 0° C. for future use.

*Reacton mix for Sau3A restriction was prepared with the following composition.
50 mM NaCl
10 mM Tris-HCl, pH 7.5
10 mM MgCl₂

C. BamHI Digestion of Plasmid pOW303

Plasmid pOW303 (prepared in Example 6) was digested in substantial accordance with the teaching of Example 6A except that plasmid pOW303 and BamHI restriction enzyme and reaction mix, rather than plasmid pOW10 and NcoI restriction enzyme and reaction mix, were used. The desired plasmid pOW303 digest was ethanol precipitated and dissolved in 10 μl. of TE.

D. Ligation and Transformation

About 2 μl. (0.1 μg.) of the ~518 bp Sau3A fragments of plasmid pOW440 and 1 μl. (0.5 μg.) of the BamHI digest of plasmid pOW303 were ligated in substantial accordance with the teaching of Example 6E. The resultant ligated DNA was used to transform *E. coli* K12 JA221 in substantial accordance with the procedures of Lederburg and Cohen, 1972 on TY plates containing 80 μg./ml. of antibiotic ampicillin. The transformants were conventionally cultured and the desired transformants identified by screening for nuclease activity and by size, restriction site and DNA sequence analysis of the constitutive plasmids. The thus identified transformants, designated as *E. coli* K12 JA221/pOW323/Z, were conventionally grown for subsequent production and isolation of plasmid pOW323/Z.

EXAMPLE 23

Construction of Plasmid pOW323 and *E. coli* K12 JA221/pOW323

A. EcoRI-PvuII Digestion of Plasmid pBR322

The desired digestion was carried out in substantial accordance with the teaching of Example 1A-2 except that PvuII, rather than SfaNI, restriction enzyme was used in the second digestion. The desired digest was conventionally extracted, ethanol precipitated and dissolved in about 10 μl. of TE.

B. EcoRI-PvuII Digestion of Plasmid pOW323/Z and Isolation of the ~0.9 kb Fragments The desired digestion and isolation were carried out in substantial accordance with the teaching of Example 1A-2 except that PvuII, rather than SfaNI, restriction enzyme was used in the second digestion. The desired ~0.9 kb EcoRI-PvuII fragments were dissolved in about 10 μl. of TE.

C. Ligation and Transformation

The desired ligation was carried out in substantial accordance with the teaching of Example 6E. The resultant ligated DNA was used to transform *E. coli* K12 JA221 in substantial accordance with the procedure of Lederburg and Cohen, 1972 on TY plates containing 80 μg./ml. of antibiotic ampicillin. The transformants were conventionally identified by screening for nuclease activity and by size, restriction and DNA sequence analysis of the constitutive plasmids. The thus identified transformants, designated as *E. coli* K12 JA221/pOW323, were conventionally grown for subsequent production and isolation of plasmid pOW323.

EXAMPLE 24

Construction of Plasmid pOW324 and *E. coli* K12 JA221/pOW324

A. NcoI Digestion of Plasmid pOW323

The desired digestion was carried out in substantial accordance with the teaching of Example 6A except that plasmid pOW323, rather than plasmid pOW10, was used.

B. Construction of the DNA Fragment

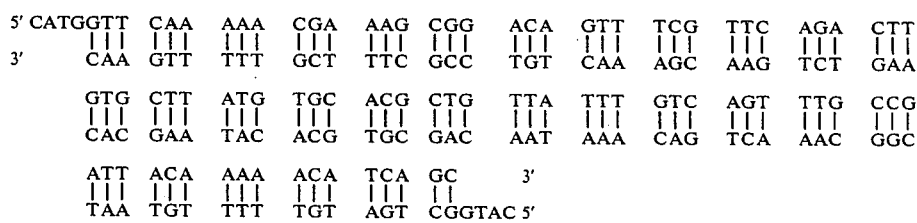

wherein
A is deoxyodenyl,
G is deoxyguanyl,
C is deoxycytosyl and
T is thymidyl.

The desired fragment was constructed using an automated phosphite triester method. Although any DNA synthesizer can be used, the DNA Synthesizer 380A of Applied Biosystems, Foster City, Calif. is preferred. Those skilled in the art will recognize that the above sequence can also be conventionally synthesized in accordance with the procedure of Itakura et al., 1977, Science 198:1056 and Crea et al., 1978, Proc. Nat. Acad. Sci. U.S.A. 75:5765. In addition, an especially preferred synthetic method is disclosed in Hsuing et al., 1983, Nucleic Acid Research 11:3227 and Narang et al, 1980, Methods in Enzymology 68:90. The desired fragment was dissolved in TE and stored at 0° C. for future use.

C. Ligation and Transformation

The desired ligation of the fragments of Example 24A and B was carried out in substantial accordance with the teaching of Example 6E. The resultant ligated DNA was used to transform *E. coli* K12 JA221 in substantial accordance with the procedure of Lederburg and Cohen, 1972 on TY plates containing 80 μg./ml. of antibiotic ampicillin. The transformants were conventionally cultured and the desired transformants identified by screening for nuclease activity and by size, restriction and DNA sequence analysis of the constitutive plasmids. The thus identified transformants, designated as *E. coli* K12 JA221/pOW324, were conventionally grown for subsequent production and isolation of plasmid pOW324.

EXAMPLE 25

Construction of Plasmid pOW441 and *E. coli* K12 JA221/POW441

A. EcoRI Digestion of Plasmid pOW324

The desired digestion was carried out in substantial accordance with the teaching of Example 2D except that about 1 μg of plasmid pOW324, rather than plasmids pOW10 and pHI-18, was used. The desired digest was dissolved in about 10 μl. of TE and stored at 0° C. for future use.

B. EcoRI Digestion of Plasmid pOW430

The bacterium *Bacillus subtilis* MI112/pOW430 (NRRL B-15833) was cultured and plasmid pOW430 isolated in substantial accordance with the teaching of Example 2. The desired plasmid pOW430 was dissolved in TE buffer and then digested with EcoRI restriction enzyme in substantial accordance with the teaching of Example 2D. The resultant digest was dissolved in about 10 μl. of TE and stored at 0° C. for future use.

C. Ligation and Transformation

The desired ligation was carried out in substantial accordance with the teaching of Example 6E. The resultant ligated DNA was used to transform *E. coli* K12 JA221 in substantial accordance with the procedure of Lederburg and Cohen, 1972 on TY plates containing 20 μg./ml. of antibiotic chloramphenicol. Transformants were screened and desired transformants identified in accordance with the procedure of Example 24C. The thus identified transformants, designated as *E. coli* K12 JA221/pOW441, were conventionally grown for subsequent production and isolation of plasmid pOW441. A restriction site map of plasmid pOW441 is presented in FIG. 6 of the accompanying drawings.

Those skilled in the art will recognize that the above procedure also generates plasmids in which the orientation of the plasmid pOW324 DNA is opposite the orientation found in plasmid pOW441. Such plasmids, including the *E coli* and Bacillus transformants thereof, are also within the scope of the present invention and can be readily identified using conventional restriction site analysis and other tests.

EXAMPLE 26

Construction of *Bacillus subtilis* MI112/pOW441

The desired construction was made in substantial accordance with the teaching of Example 2C except that plasmid pOW441, rather than plasmid pHI-18, was used. The thus constructed transformants express Staphylococcus nuclease intracellularly and also secrete nuclease into the culture medium. For screening transformants, individual colonies were picked and scratched on TB-D plates (Shortle, 1983, Gene 22:181) followed by incubation at 37° C. for 1-16 hours. Broth cultures were generally assayed at late logrithmic growth phase (330-370 Klett units 54 filter). Thirty μl. samples were spotted into wells (5 mm diameter) cut into immunodiffusion plates (Miles Laboratories, Elkhart, Ind.) of TB-D agar (10 ml., 1.8 mm depth). Incubation at 37° C. for 1-2 hours was sufficient for determining, as indicated by the formation of halos, positive nuclease producers. Cell extracts and medium were also assayed for nuclease activity in substantial accordance with the procedure of Cuatrecasas et al., 1967, J. Biol. Chem. 25:6544, except that all assays were performed at ambient temperature.

EXAMPLE 27

Construction of Plasmid pOW445 and *E. coli* K12 JA221/pOW445

A. EcoRI Digestion of Plasmid pOW323

The desired digestion was carried out in substantial accordance with the teaching of Example 2D except that about 2 μl. (1 μg.) of plasmid pOW323, rather than plasmids pOW10 and pHI-18, were used. The desired digest was dissolved in about 10 μl. of TE and stored at 0° C. for future use.

B. Ligation and Transformation

The EcoRI-digested plasmids pOW430 (prepared in Example 25B) and pOW323 were ligated in substantial accordance with the teaching of Example 6E. The resultant ligated DNA was used to transform *E. coli* K12 JA221 in substantial accordance with the procedure of Lederburg and Cohen, 1972 on TY plates containing 20 μg./ml. of antibiotic chloramphenicol. Transformants were screened and desired transformants identified in accordance with the procedure of Example 24C. The thus identified transformants, designated as *E. coli* K12 JA221/pOW445, were grown for subsequent production and isolation of plasmid pOW445. A restriction site map of plasmid pOW445 is presented in FIG. 7 of the accompanying drawings.

Those skilled in the art will recognize that the above procedure also generates plasmids in which the orientation of the plasmid pOW323 DNA is opposite the orientation found in plasmid pOW445. Such plasmids, including the *E. coli* and Bacillus transformants thereof, are also within the scope of the present invention and can be readily identified using conventional restriction site analysis and other tests.

EXAMPLE 28

Construction of *Bacillus subtilis* MI112/pOW445

The desired construction was made in substantial accordance with the teaching of Example 2C except that plasmid pOW445, rather than plasmid pHI-18, was used. The thus constructed transformants express Staphylococcus nuclease intracellularly. Nuclease expression was determined by the method previously described in Example 26.

EXAMPLE 29

Efficiency of Expression and Secretion of Nuclease

Production of nuclease was improved by using a minimal salts medium fortified with amino acids and with glycerol and citrate as carbon sources. Such improved production may be due to the fact that bacilli secrete higher levels of protein under conditions that limit growth and that protease production is reduced when amino acids are added to the medium. The level of nuclease appeared to be dependent on the concentration of sodium ions in the medium. Although levels of one percent improved expression and secretion of nuclease, increasing the sodium ion content to two percent either as sodium citrate or sodium chloride decreased the level of nuclease activity in the culture supernatant.

We claim:

1. A novel recombinant DNA expression vector which comprises
   (1) the ribosome binding site-containing DNA sequence

wherein
   A is deoxyadenyl,
   G is deoxyguanyl,
   C is deoxycytosyl,
   T is thymidyl,
   R is G or C, and
   $R^1$ is G or C,
   (2) the veg promoter of *Bacillus subtilis*, and
   (3) a gene that encoes a functional polypeptide, subject to the limitation that R and $R^1$ are not simultaneously the same deoxyribonucleotide and subject to the further limitation that said vector is selectable and that said promoter and said DNA sequence direct transcription and expression of said gene in a host cell transformed by said vector.

2. The expression vector of claim 1 which is a plasmid.

3. The expression vector of claim 2 wherein the gene that encodes a functional polypeptide is selected from the group consisting of genes that encode human pre-proinsulin, human proinsulin, human insulin A-chain, human insulin B-chain, non-human insulin, human growth hormone, non-human growth hormone, bovine growth hormone, porcine growth hormone, human interferon, non-human inteferon, viral antigen, urokinase, hormones and enzymes.

4. The expression vector of claim 3 in which the gene encodes human pre-proinsulin.

5. The expression vector of claim 3 in which the gene encodes human proinsulin.

6. The expression vector of claim 3 in which the gene encodes human insulin A-chain.

7. The expression vector of claim 3 in which the gene encodes human insulin B-chain.

8. The expression vector of claim 3 in which the gene encodes non-human insulin.

9. The expression vector of claim 3 in which the gene encodes human growth hormone.

10. The expression vector of claim 3 in which the gene encodes non-human growth hormone.

11. The expression vector of claim 3 in which the gene encodes bovine growth hormone.

12. The expression vector of claim 3 in which the gene encodes porcine growth hormone.

13. The expression vector of claim 3 in which the gene encodes human interferon.

14. The expression vector of claim 3 in which the gene encodes viral antigen.

15. The expression vector of claim 3 in which the gene encodes a hormone.

16. The expression vector of claim 3 in which the gene encodes an enzyme.

17. The expression vector of claim 1 which is selected from the group consisting of plasmids pOW10, pOW303, pOW523, pOW524, POW525, pOW526, pOW527, pOW528, pOW529, pOW530, pOW11, pOW531, pOW532, pOW533, pOW534, pOW310, pOW535, pOW536, pOW537 and pOW538.

18. The expression vector of claim 17 which is pOW10.

19. The expression vector of claim 17 which is pOW303.

20. The expression vector of claim 17 which is pOW523.

21. The expression vector of claim 17 which is pOW524.

22. The expression vector of claim 17 which is pOW525.

23. The expression vector of claim 17 which is pOW526.

24. The expression vector of claim 17 which is pOW527.

25. The expression vector of claim 17 which is pOW528.

26. The expression vector of claim 17 which is pOW529.

27. The expression vector of claim 17 which is pOW530.

28. The DNA sequence of claim 1 which is

wherein
A is deoxyadenyl,
G is deoxyguanyl,
C is deoxycytosyl,
T is thymidyl,
R is G or C and
$R^1$ is G or C,
subject to the limitation that R and $R^1$ are not simultaneously the same deoxyribonucleotide.

29. A transformed host cell comprising a recombinant DNA expression vector of claim 1.

30. The transformed host cell of claim 29 which is Bacillus.

31. The transformed host cell of claim 30 which is *Bacillus subtilis*.

32. The transformed host cell of claim 29 which is *E. coli*.

33. The transformed host cell of claim 31 wherein the gene that encodes a functional polypeptide is selected from the group consisting of genes that encode human pre-proinsulin, human proinsulin, human insulin A-chain, human insulin B-chain, non-human insulin, human growth hormone, non-human growth hormone, bovine growth hormone, porcine growth hormone, human interferon, non-human interferon, viral antigen, urokinase, hormones and enzymes.

34. The transformed host cell of claim 33 in which the gene encodes human pre-proinsulin.

35. The transformed host cell of claim 33 in which the gene encodes human proinsulin.

36. The transformed host cell of claim 33 in which the gene encodes human insulin A-chain.

37. The transformed host cell of claim 33 in which the gene encodes human insulin B-chain.

38. The transformed host cell of claim 33 in which the gene encodes human growth hormone.

39. The transformed host cell of claim 33 in which the gene encodes bovine growth hormone.

40. The transformed host cell of claim 33 in which the gene encodes porcine growth hormone.

41. A transformed host cell comprising a recombinant DNA expression vector of claim 17.

42. The transformed host cell of claim 30 wherein the recombinant DNA expression vector is selected from the group consisting of plasmids pOW523, pOW524, POW525, pOW526, pOW527, pOW528, pOW529, pOW530, pOW531, pOW532, pOW533, pOW534, pOW535, pOW536, pOW537 and pOW538.

43. The transformed host cell of claim 41 which is *E. coli*.

44. The transformed host cell of claim 42 which is *Bacillus subtilis*.

45. The transformed host cell of claim 44 which is *Bacillus subtilis* MI112/pOW523.

46. The transformed host cell of claim 44 which is *Bacillus subtilis* MI112/pOW524.

47. The transformed host cell of claim 44 which is *Bacillus subtilis* MI112/pOW525.

48. The transformed host cell of claim 44 which is *Bacillus subtilis* MI112/pOW526.

49. The transformed host cell of claim 44 which is *Bacillus subtilis* MI112/pOW527.

50. The transformed host cell of claim 44 which is *Bacillus subtilis* MI112/pOW528.

51. The transformed host cell of claim 44 which is *Bacillus subtilis* MI112/pOW529.

52. The transformed host cell of claim 44 which is *Bacillus subtilis* MI112/pOW530.

53. A method for producing a functional polypeptide in Bacillus wherein said polypeptide is secreted into the culture medium, said method comprises transforming a Bacillus host cell with a recombinant DNA expression vector which comprises
   (1) the ribosome binding site-containing DNA sequence

```
5' A G T G A G G T G G A T R  C     3'
   | | | | | | | | | | |
3'           T C C A C C T A R¹ G G T A C 5'
``` wherein

A is deoxyadenyl,
G is deoxyguanyl,
C is deoxycytosyl,
T is thymidyl,
R is G or C, and
R¹ is G or C (2) the veg promoter of *Bacillus subtilis*, and
(3) a gene that encodes a signal peptide-containing functional polypeptide, and culturing said transformed Bacillus host cell under growth conditions, subject to the limitation that R and R¹ are not simultaneously the same deoxyribonucleotide and subject to the further limitation that said vector is selectable and that said promoter and said DNA sequence direct transcription and expression of said gene in said transformed Bacillus cell.

54. The method of claim 53 wherein the expression vector is a plasmid and the host cell is *Bacillus subtilis*.

55. The method of claim 54 wherein the gene that encodes a signal peptide-containing polypeptide is selected from the group of genes consisting of genes that encode human pre-proinsulin, pre-growth hormone, pre-bovine growth hormone, pre-human growth hormone, pre-porcine growth hormone, immune modulators, proteolytic degradative enzymes, and cellulolytic degradative enzymes.

56. The method of claim 55 in which the gene encodes human pre-proinsulin.

57. The method of claim 55 in which the gene encodes pre-growth hormone.

58. The method of claim 55 in which the gene encodes pre-bovine growth hormone.

59. The method of claim 55 in which the gene encodes pre-porcine growth hormone.

60. The method of claim 55 in which the gene encodes pre-human growth hormone.

61. The method of claim 53 wherein the expression vector is selected from the group of plasmids consisting of plasmids pOW525, pOW526, pOW527, pOW528, POW531, pOW532, pOW533 and pOW534.

62. The method of claim 61 wherein the host cell is *Bacillus subtilis*.

63. The method of claim 62 in which the host cell is *Bacillus subtilis* MI112/pOW525.

64. The method of claim 62 in which the host cell is *Bacillus subtilis* MI112/pOW526.

65. The method of claim 62 in which the host cell is *Bacillus subtilis* MI112/pOW527.

66. The method of claim 62 in which the host cell is *Bacillus subtilis* MI112/pOW528.

67. The expression vector of claim 17 which is plasmid pOW11.

68. The expression vector of claim 17 which is plasmid pOW310.

69. The expression vector of claim 17 which is plasmid pOW531.

70. The expression vector of claim 17 which is plasmid pOW533.

71. The expression vector of claim 17 which is plasmid pOW535.

72. The expression vector of claim 17 which is plasmid pOW537.

73. The transformed host cell of claim 42 which is *Bacillus subtilis* MI112/pOW531.

74. The transformed host cell of claim 42 which is *Bacillus subtilis* MI112/pOW533.

75. The transformed host cell of claim 42 which is *Bacillus subtilis* MI112/pOW535.

76. The transformed host cell of claim 43 which is *Bacillus subtilis* MI112/pOW537.

77. The method of claim 61 wherein the host cell is *Bacillus subtilis* MII12/pOW531.

78. The method of claim 61 wherein the host cell is *Bacillus subtilis* MI112/pOW533.

79. An expression vector selected from the group consisting of plasmids pOW323/Z, pOW323, pOW324, pOW441 and pOW445.

80. The vector of claim 79 which is pOW323.

81. The vector of claim 77 which is pOW441.

82. The vector of claim 79 which is pOW445.

83. A transformed host cell comprising an expression vector of claim 79.

84. The transformed host cell of claim 83 which is selected from the group consisting of *E. coli* and *Bacillus subtilis* and wherein the plasmid is selected from the group consisting of pOW441 and pOW445.

85. The transformed host cell of claim 84 which is *Bacillus subtilis* MI112/pOW441.

86. The transformed host cell of claim 84 which is *Bacillus subtilis* MI112/pOW445.

87. The method of claim 53 wherein the expression vector is pOW441.

* * * * *

UNITED STATES PATENT AND TRADEMARK OFFICE
CERTIFICATE OF CORRECTION

PATENT NO. : 4,783,405

DATED : November 8, 1988

INVENTOR(S) : Kovacevic, et al.

It is certified that error appears in the above-identified patent and that said Letters Patent is hereby corrected as shown below:

Claim 28, line 50, delete "of Claim 1".

Claim 76, line 3, "43" should read -- 42 --.

Claim 81, line 13, "77" should read -- 79 --.

Signed and Sealed this

Eighteenth Day of July, 1989

Attest:

DONALD J. QUIGG

Attesting Officer

Commissioner of Patents and Trademarks